US011873396B2

(12) United States Patent
Macfarlane et al.

(10) Patent No.: US 11,873,396 B2
(45) Date of Patent: Jan. 16, 2024

(54) NANOSTRUCTURES FOR THE ASSEMBLY OF MATERIALS

(71) Applicant: Massachusetts Institute of Technology, Cambridge, MA (US)

(72) Inventors: Robert J. Macfarlane, Cambridge, MA (US); Jianyuan Zhang, Cambridge, MA (US); Peter Jeffries Santos, Cambridge, MA (US); Paul Anthony Gabrys, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 232 days.

(21) Appl. No.: 17/394,964

(22) Filed: Aug. 5, 2021

(65) Prior Publication Data

US 2022/0033639 A1     Feb. 3, 2022

Related U.S. Application Data

(62) Division of application No. 16/335,483, filed as application No. PCT/US2017/052787 on Sep. 21, 2017, now Pat. No. 11,118,048.

(60) Provisional application No. 62/397,684, filed on Sep. 21, 2016.

(51) Int. Cl.
| C08L 51/00 | (2006.01) |
| C08L 51/10 | (2006.01) |
| B82Y 5/00 | (2011.01) |
| B82Y 40/00 | (2011.01) |
| C08K 3/16 | (2006.01) |
| C08K 3/22 | (2006.01) |

(52) U.S. Cl.
CPC .............. *C08L 51/10* (2013.01); *C08L 51/00* (2013.01); *B82Y 5/00* (2013.01); *B82Y 40/00* (2013.01); *C08F 2438/00* (2013.01); *C08K 3/16* (2013.01); *C08K 3/22* (2013.01); *C08L 2207/53* (2013.01)

(58) Field of Classification Search
CPC ...... C08L 51/10; C08L 2207/53; C08L 51/00; C08K 3/16; C08K 3/22; B82Y 5/00; B82Y 40/00; C08F 2438/00
USPC ........................................................ 523/201
See application file for complete search history.

(56) References Cited

U.S. PATENT DOCUMENTS

| 6,291,021 | B1 | 9/2001 | Morita |
| 8,008,395 | B2 | 8/2011 | Zoromski |
| 11,118,048 | B2* | 9/2021 | Macfarlane ............. C08L 51/10 |
| 2002/0115747 | A1 | 8/2002 | Feldheim et al. |
| 2003/0092838 | A1* | 5/2003 | Fomperie ............. H01B 3/441 525/71 |
| 2005/0142030 | A1 | 6/2005 | Kim et al. |
| 2007/0112101 | A1 | 5/2007 | Choi et al. |
| 2009/0208580 | A1 | 8/2009 | Shi et al. |
| 2011/0105643 | A1 | 5/2011 | Chun et al. |
| 2013/0237408 | A1 | 9/2013 | Pinkhassik et al. |
| 2014/0308529 | A1* | 10/2014 | Hardinghaus .......... C09D 5/006 428/447 |
| 2015/0314941 | A1 | 11/2015 | Ramadas et al. |
| 2016/0088756 | A1 | 3/2016 | Ramadas et al. |

OTHER PUBLICATIONS

International Preliminary Report on Patentability dated Apr. 4, 2019 for Application No. PCT/US2017/052787.
International Search Report and Written Opinion dated Dec. 11, 2017 for Application No. PCT/US2017/052787.
Adler-Abramovich et al., The physical properties of supramolecular peptide assemblies: from building block association to technological applications. ChemSoc Rev. Sep. 22, 2014;43(20):6881-93. Epub Aug. 6, 2014.
Alexeev et al., Photonic crystal glucose-sensing material for non-invasive monitoring of glucose in tear fluid. Clin Chem. Dec. 2004;50(12):2353-60. Epub Sep. 30, 2004.
Alivisatos et al., Organization of 'nanocrystal molecules' using DNA. Nature. Aug. 15, 1996;382(6592):609-11.
Balazs et al., Nanoparticle polymer composites: where two small worlds meet. Science. Nov. 17, 2006;314(5802):1107-10.
Bates et al., Polarity-switching top coats enable orientation of sub-10-nm block copolymer domains. Science. Nov. 9, 2012;338(6108):775-9.
Beaulieu et al., Large-area printing of optical gratings and 3D photonic crystals using solution-processable nanoparticle/polymer composites. ACS Photon. Aug. 18, 2014;1(9):799-805. Epub Aug. 11, 2014.
Bertrand et al., Routes to Hydrogen Bonding Chain-End Functionalized Polymers. Macromol Rapid Commun. Dec. 21, 2012;33(24):2062-91. Epub Nov. 7, 2012.
Bertrand et al., Straightforward preparation of telechelic H-bonding polymers from difunctional trithiocarbonates and supramolecular block copolymers thereof. Macromolecules. Apr. 29, 2011;44(10):3694-704.
Boal et al., Self-assembly of nanoparticles into structured spherical and network aggregates. Nature. Apr. 13, 2000;404(6779):746-8.

(Continued)

*Primary Examiner* — Hannah J Pak
(74) *Attorney, Agent, or Firm* — Wolf, Greenfield & Sacks, P.C.

(57) ABSTRACT

Nanostructures and associated compositions, systems, and methods are provided. In some embodiments, a nanostructure may comprise polymers, intermolecular bonding groups, and a particle. The polymers may be associated with the particle and the intermolecular bonding groups may be associated with at least some of the polymers. In some embodiments, at least some of the intermolecular bonding groups may have a different chemical composition and/or chemical property than the polymers. In some embodiments, nanostructures may reversibly associate with each other via the intermolecular bonding groups to form a material. In some such cases, the intermolecular bonding groups on different nanostructures may reversibly associate with each other. In some embodiments, the nanostructures may be designed, such that the energy required to disassociate at least a portion of the nanostructures in the material is greater than the energy required to dissociate a single association between intermolecular bonding groups.

20 Claims, 19 Drawing Sheets

(56) References Cited

OTHER PUBLICATIONS

Boles et al., Self-assembly of colloidal nanocrystals: From intricate structures to functional materials. Chem Rev. Aug. 23, 2016;116(18):11220-89.
Brechet et al., Polymer Based Nanocomposites: Effect of Filler-Filler and Filler-Matrix Interactions. Adv Eng Mater. Aug. 2001;3(8):571-7.
Cheon et al., Magnetic Superlattices and their nanoscale phase transition effects. Proc Natl Acad Sci U S A. Feb. 28, 2006;103(9):3023-7.
Chiu et al., Control of nanoparticle location in block copolymers. J Am Chem Soc. Apr. 13, 2005;127(14):5036-7. Epub Mar. 19, 2005.
Choi et al., Flexible particle array structures by controlling polymer graft architecture. J Am Chem Soc. Aug. 20, 2010;132(36):12537-9.
Choi et al., Toughening fragile matter: mechanical properties of particle solids assembled from polymer-grafted hybrid particles synthesized by ATRP. Soft Matter. Mar. 2012;8(15):4072-82. Epub Feb. 1, 2012.
Crosby et al., Polymer nanocomposites: the "nano" effect on mechanical properties. Polymer Rev. Apr. 1, 2007;47(2):217-29. Epub Apr. 26, 2007.
Daniel et al., Gold nanoparticles: assembly, supramolecular chemistry, quantum-size-related properties, and applications toward biology, catalysis, and nanotechnology. Chem Rev. Jan. 14, 2004;104(1):293-346. Epub Dec. 20, 2003.
Deans et al., Recognition-Mediated Unfolding of a Self-Assembled Polymeric Globule. Macromolecules. Jul. 2, 1999;32(15):4956-60.
Elacqua et al., Engineering orthogonality in supramolecular polymers: From simple scaffolds to complex materials. Acc Chem Res. Jun. 6, 2014;47(8):2405-16.
Gao et al., Self-orienting nanocubes for the assembly of plasmonic nanojunctions. Nat Nanotechnol. Jul. 2012;7:433-7. Epub Jun. 10, 2012.
Ghosh et al., Nanostructured conducting polymers for energy applications: towards a sustainable platform. Nanoscale. Mar. 2016;8(13):6921-47.
Goulet et al., Facile phase transfer of large, water-soluble metal nanoparticles to nonpolar solvents. Langmuir. Jan. 27, 2012;28(5):2909-13.
Hashemi et al., Enhanced glassy state mechanical properties of polymer nanocomposites via supramolecular interactions. Nano Lett. Jul. 24, 2015;15(8):5465-71. Epub Jul. 20, 2015.
Hatton et al., Assembly of large-area, highly ordered, crack-free inverse opal films. Proc Natl Acad Sci U S A. Jun. 8, 2010;107(23):10354-9.
Heo et al., Thermally reversible aggregation of Gold nanoparticles in polymer nanocomposites through hydrogen bonding. Nano Lett. Oct. 28, 2013;13(11):5297-302.
Hosseini, Molecular tectonics: from simple tectons to complex molecular networks. Acc Chem Res. Apr. 19, 2005;38(4):313-23. Epub Jan. 15, 2005.
Huang et al., Immobilization of semisoft colloidal crystals formed by polymer-brush-afforded hybrid particles. Langmuir. Jun. 17, 2014;30(25):7304-12. Epub Jun. 2, 2014.
Hui et al., Surface-initiated polymerization as an enabling tool for multifunctional (nano-) engineered hybrid materials. Chem Mater. 2014;26(1):745-62. Epub Aug. 14, 2013.
Jang et al., Controlled supramolecular assembly of micelle-like gold nanoparticles in PS-b-P2VP diblock copolymers via hydrogen bonding. J Am Chem Soc. Oct. 26, 2011;133(42):16986-96. doi: 10.1021/ja206615c. Epub Oct. 4, 2011.
Jang et al., Morphology evolution of PS-b-P2VP diblock copolymers via supramolecular assembly of hydroxylated gold nanoparticles. Macromolecules. Jan. 20, 2012;45(3):1553-61.
Jones et al., DNA-nanoparticle superlattices formed from anisotropic building blocks. Nat Mater. Nov. 2010;9(11):913-7. Epub Oct. 3, 2010.
Jones et al., Programmable materials and the nature of the DNA bond. Science. Feb. 20, 2015;347(6224): 1260901(1-11).

Jones et al., Templated techniques for the synthesis and assembly of plasmonic nanostructures. Chem Rev. Jun. 8, 2011;111(6):3736-827. doi: 10.1021/cr1004452.
Kalsin et al., Electrostatic self-assembly of binary nanoparticle crystals with a diamond-like lattice. Science. Apr. 21, 2006;312(5772):420-4. Epub Feb. 23, 2006.
Kango et al., Surface modification of inorganic nanoparticles for development of organic-inorganic nanocomposites—A review. Prog Polym Sci. Aug. 1, 2013;38(8):1232-61. Epub Mar. 7, 2013.
Kao et al., Rapid fabrication of hierarchically structured supramolecular nanocomposite thin films in one minute. Nat Commun. Jun. 2, 2014;5:4053(1-8). doi: 10.1038/ncomms5053.
Kelly et al., The optical properties of metal nanoparticles: the influence of size, shape, and dielectric environment. J Phys Chem B. Jan. 1, 2003;107:668-77. Epub Dec. 21, 2002.
Kim et al., Inorganic nanoparticles in porous coordination polymers. Chem Soc Rev. Apr. 6, 2016;45(14):3828-45. Epub Feb. 4, 2016.
Ku et al., Self-assembly of magnetic nanoparticles in evaporating solution. J Am Chem Soc. Feb. 2, 2011;133(4):838-48. doi: 10.1021/ja107138x. Epub Dec. 15, 2010.
Kumar et al., Nanocomposites with polymer grafted nanoparticles. Macromolecules. Apr. 23, 2013;46(9):3199-214.
Li et al., Flexible high-temperature dielectric materials from polymer nanocomposites. Nature. Jul. 30, 2015;523(7562):576-9. doi: 10.1038/nature14647. Erratum in: Nature. Aug. 4, 2016;536(7614):112.
Li et al., Thermally active hybridization drives the crystallization of DNA-functionalized nanoparticles. J Am Chem Soc. May 21, 2013;135(23):8535-41. Epub May 12, 2013.
Lin et al., High Ionic Conductivity of Composite Solid Polymer Electrolyte via in Situ Synthesis of Monodispersed SiO2 Nanospheres in Poly(ethylene oxide). Nano Lett. Jan. 13, 2016;16(1):459-65. doi: 10.1021/acs.nanolett.5b04117. Epub Nov. 23, 2015.
Lin et al., Linker-Mediated Self-Assembly Dynamics of Charged Nanoparticles. ACS Nano. Aug. 23, 2016;10(8):7443-50. doi: 10.1021/acsnano.6b01721. Epub Aug. 5, 2016.
Luk'yanchuk et al., The Fano resonance in plasmonic nanostructures and metamaterials. Nat Mater. Sep. 2010;9(9):707-15. doi: 10.1038/nmat2810. Epub Aug. 23, 2010.
Macfarlane et al., Establishing the design rules for DNA-mediated programmable colloidal crystallization. Angew Chem Int Ed. Jun. 21, 2010;49(27):4589-92. Epub Jun. 16, 2010.
Macfarlane et al., Nanoparticle superlattice engineering with DNA. Science. Oct. 14, 2011;334(6053):204-8. doi: 10.1126/science.1210493.
Macfarlane et al., Nucleic acid-modified nanostructures as programmable atom equivalents: forging a new "table of elements". Angew Chem Int Ed. May 27, 2013;52(22):5688-98. Epub May 2, 2013.
Matyjaszewski et al., Nanostructured functional materials prepared by atom transfer radical polymerization. Nat Chem. Jul. 2009;1(4):276-88. Epub Jun. 22, 2009.
Matyjaszewski, Atom transfer radical polymerization (ATRP): current status and future perspectives. Macromolecules. Apr. 11, 2012;45(10):4015-39.
O'Brien et al., Universal noble metal nanoparticle seeds realized through iterative reductive growth and oxidative dissolution reactions. J Am Chem Soc. May 15, 2014;136(21):7603-6.
O'Dwyer, Color-Coded Batteries-Electro-Photonic Inverse Opal Materials for Enhanced Electrochemical Energy Storage and Optically Encoded Diagnostics. Adv Mater. Jul. 2016;28(27):5681-8. Epub Jan. 19, 2016.
Ohno et al., Suspensions of Silica Particles Grafted with Concentrated Polymer Brush: Effects of Graft Chain Length on Brush Layer Thickness and Colloidal Crystallization. Macromolecules. Nov. 16, 2007;40(25):9143-50.
Paik et al., Binary and ternary superlattices self-assembled from colloidal nanodisks and nanorods. J Am Chem Soc. May 15, 2015;137(20):6662-9. Epub Apr. 30, 2015.
Paul et al., Polymer nanotechnology: nanocomposites. Polymer. Jul. 7, 2008;49(15):3187-204. Epub Apr. 13, 2008.
Quan et al., Solvent-mediated self-assembly of nanocube superlattices. J Am Chem Soc. Jan. 29, 2014;136(4):1352-9. doi: 10.1021/ja408250q. Epub Jan. 3, 2014.

(56) References Cited

OTHER PUBLICATIONS

Rinne et al., Embedded cavities and waveguides in three-dimensional silicon photonic crystals. Nat Photon. Jan. 2008;2(1):52-6. Epub Dec. 2007.
Ross et al., Using nanoscale and mesoscale anisotropy to engineer the optical response of three-dimensional plasmonic metamaterials. Nat Commun. Jun. 17, 2014;5:4090(1-11).
Rybtchinski, Adaptive supramolecular nanomaterials based on strong noncovalent interactions. ACS Nano. Sep. 8, 2011;5(9):6791-818. Epub Aug. 26, 2011.
Shafiei et al., A subwavelength plasmonic metamolecule exhibiting magnetic-based optical Fano resonance. Nat Nanotechnol. Feb. 2013;8:95-9. Epub Jan. 27, 2013.
Shevchenko et al., Structural diversity in binary nanoparticle superlattices. Nature. Jan. 5, 2006;439(7072):55-9.
Shibu et al., Gold nanoparticle superlattices as functional solids for concomitant conductivity and SERS tuning. Nanoscale. 2011;3(3):1066-72.
Sing et al., Electrostatic control of block copolymer morphology. Nat Mater. Jul. 2014;13(7):694-8. Epub Jun. 8, 2014.
Stauffer et al., Bright Stretchable Alternating Current Electroluminescent Displays Based on High Permittivity Composites. Adv Mater. Sep. 2016;28(33):7200-3. doi: 10.1002/adma.201602083. Epub Jun. 14, 2016.
Storhoff et al., What controls the optical properties of DNA-linked gold nanoparticle assemblies?. J Am Chem Soc. May 17, 2000;122(19):4640-50. Epub Apr. 25, 2000.
Sun et al., pH-Controlled reversible assembly and disassembly of gold nanorods. Small. Sep. 2008;4(9): 1287-92. doi: 10.1002/smll.200800099. Epub Aug. 6, 2008.
Takeoka, Stimuli-responsive opals: colloidal crystals and colloidal amorphous arrays for use in functional structurally colored materials. J Mat Chem C. Jul. 2, 2013;1(38):6059-74.
Talapin et al., Prospects of colloidal nanocrystals for electronic and optoelectronic applications. Chem Rev. 2010;110(1):389-458. Epub Dec. 3, 2009.
Talapin et al., Seeded growth of highly luminescent CdSe/CdS nanoheterostructures with rod and tetrapod morphologies. Nano Lett. Oct. 10, 2007;7(10):2951-9. Epub Sep. 11, 2007.
Tang et al., Evolution of block copolymer lithography to highly ordered square arrays. Science. Oct. 17, 2008;322(5900):429-32. Epub Sep. 25, 2008.
Turkevich et al., A study of the nucleation and growth processes in the synthesis of colloidal gold. J Discuss Faraday Soc. Jan. 1, 1951;11:55-75.
Urban et al., Synergism in binary nanocrystal superlattices leads to enhanced p-type conductivity in self-assembled PbTe/Ag 2 Te thin films. Nat Mater. Feb. 2007;6(2):115-21. Epub Jan. 21, 2007.
Wang et al., Molecular tectonics. Three-dimensional organic networks with zeolitic properties. J Am Chem Soc. Dec. 1994;116(26):12119-20.
Wang et al., Synthetic strategies toward DNA-coated colloids that crystallize. J Am Chem Soc. Aug. 12, 2015;137(33):10760-6. Epub Jul. 20, 2015.
Whitesides et al., Self-assembly at all scales. Science. Mar. 29, 2002;295(5564):2418-21.
Williams et al., Mechanically Robust and Self-Healable Superlattice Nanocomposites by Self-Assembly of Single-Component "Sticky" Polymer-Grafted Nanoparticles. Adv Mater. Jul. 2015;27(26):3934-41. Epub May 27, 2015.
Wu et al., Functional oligomers for the control and fixation of spatial organization in nanoparticle assemblies. J Am Chem Soc. Mar. 19, 2008;130(11):3516-20. Epub Feb. 26, 2008.
Yan et al., Self-assembly of chiral nanoparticle pyramids with strong R/S optical activity. J Am Chem Soc. Sep. 4, 2012;134(36):15114-21. Epub Aug. 19, 2012.
Ye et al., Structural diversity in binary superlattices self-assembled from polymer-grafted nanocrystals. Nat Commun. Dec. 2, 2015;6:10052(1-10).
Yetisen et al., Nanotechnology in Textiles. ACS Nano. Mar. 22, 2016;10(3):3042-68. doi: 10.1021/acsnano.5b08176. Epub Feb. 26, 2016.
Zhang et al., Hybridization of inorganic nanoparticles and polymers to create regular and reversible self-assembly architectures. Chem Soc Rev. Sep. 21, 2012;41(18):6066-88. doi: 10.1039/c2cs35038f. Epub May 28, 2012.
Zhang et al., Self-Assembling Nanocomposite Tectons. J Am Chem Soc. Dec. 21, 2016;138(50):16228-16231. doi: 10.1021/jacs.6b11052. Epub Dec. 7, 2016.
Zhao et al., Reversible trapping and reaction acceleration within dynamically self-assembling nanoflasks. Nat Nanotechnol. Jan. 2016;11(1):82-8. doi: 10.1038/nnano.2015.256. Epub Nov. 23, 2015.
Zhao et al., Small-molecule-directed nanoparticle assembly towards stimuli-responsive nanocomposites. Nat Mater. Dec. 2009;8(12):979-85. Epub Oct. 18, 2009.
Zhou et al., Self-Assembled Nanocomposite of Silicon Nanoparticles Encapsulated in Graphene through Electrostatic Attraction for Lithium-Ion Batteries. Adv Energy Mater. Apr. 30, 2012;2(9):1086-90.
Zou et al., Polymer/silica nanocomposites: preparation, characterization, properties, and applications. Chem Rev. Aug. 23, 2008;108(9):3893-957.

* cited by examiner

FIG. 7A
FIG. 7B
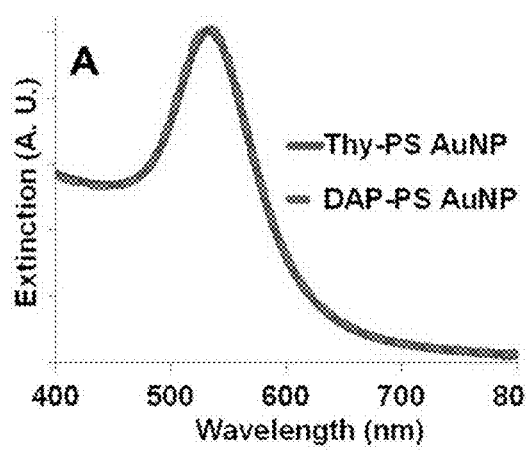
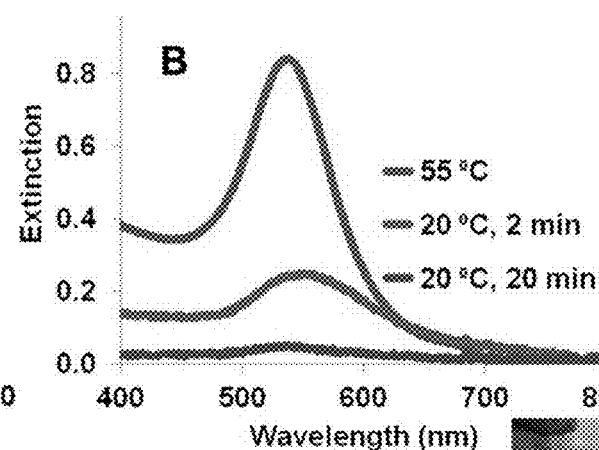
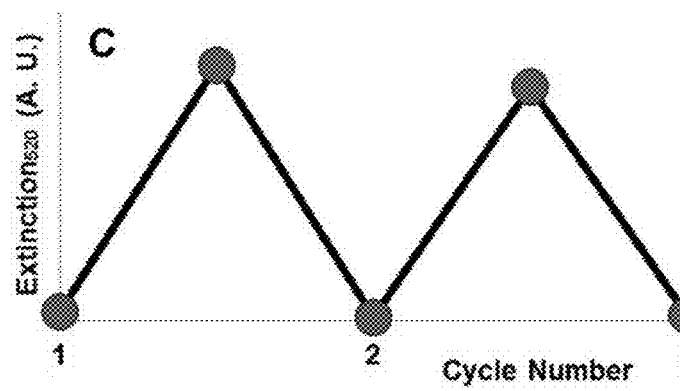
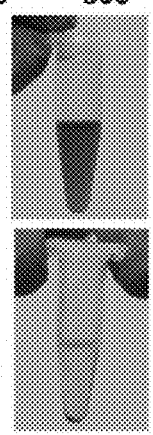
FIG. 7C

FIG. 17A
FIG. 17B
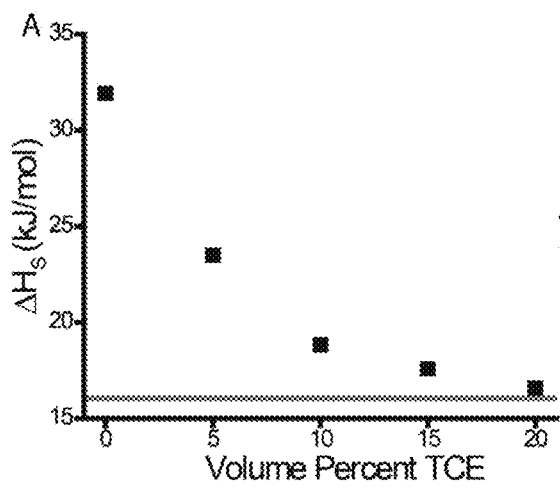
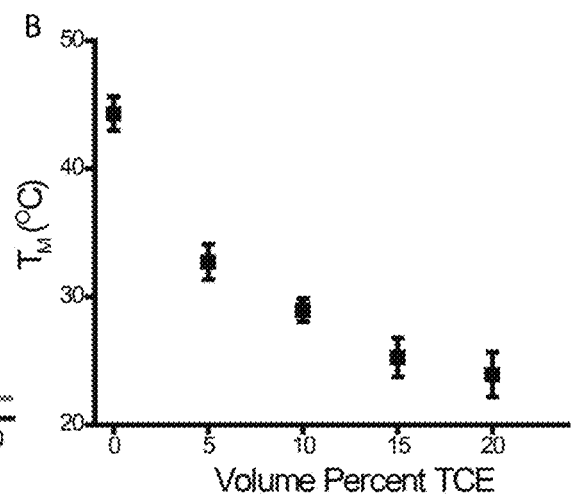
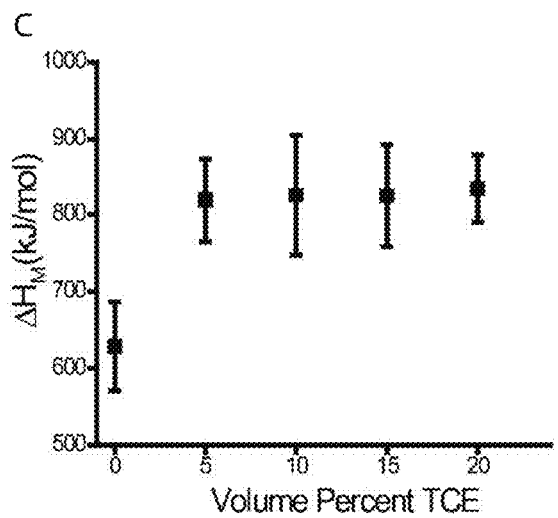
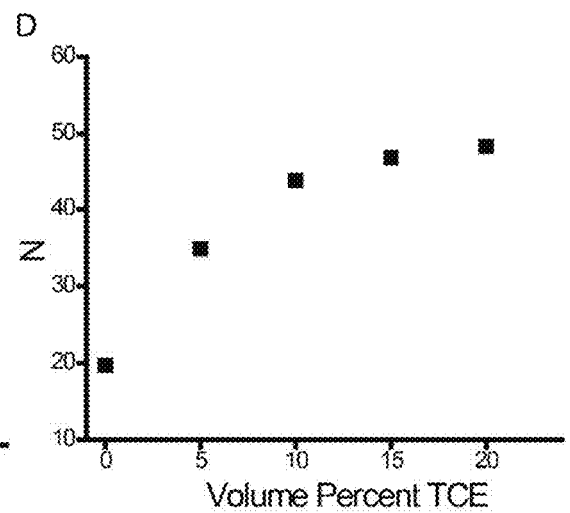
FIG. 17C
FIG. 17D

NANOSTRUCTURES FOR THE ASSEMBLY OF MATERIALS

RELATED APPLICATIONS

This application is a divisional of U.S. patent application Ser. No. 16/335,483, filed Mar. 21, 2019, entitled "Nanostructures for the Assembly of Materials", which is a national stage filing under 35 U.S.C. 371 of International Patent Application Serial No. PCT/US2017/052787, filed Sep. 21, 2017, entitled "Nanostructures for the Assembly of Materials", which claims priority under 35 U.S.C. § 119(e) to U.S. Provisional Patent Application Ser. No. 62/397,684, filed Sep. 21, 2016, and entitled "Self-Assembling Nanocomposite Tectons," each of which is incorporated herein by reference in its entirety for all purposes.

STATEMENT OF GOVERNMENT SUPPORT

This invention was made with Government support under FA9550-11-1-0275 awarded by the Air Force Office of Scientific Research. The Government has certain rights in the invention.

TECHNICAL FIELD

Nanostructures for the assembly of materials and associated compositions, systems, and methods are generally described.

BACKGROUND

A composite material is composed of two or more components that have different chemical and/or physical properties. In general, composite materials have distinct properties from the components that form the composite, even though they remain separate and/or distinct within the composite material. Much research has focused on the design of composite materials with beneficial electrical, chemical, and optical properties for application in batteries, optical sensors, optical displays, and solar energy, amongst others. Nanostructures are an attractive option for the formation of composite materials. However, current nanostructures capable of forming materials do not allow for the ordered structural organization of all components and/or utilize processing conditions that are not amenable to generating functionally useful composite structures. Accordingly, improved compositions and methods are needed.

SUMMARY

Nanostructures for the assembly of materials and associated compositions, systems, and methods are provided. The subject matter of the present invention involves, in some cases, interrelated products, alternative solutions to a particular problem, and/or a plurality of different uses of one or more systems and/or articles.

In one set of embodiments, articles are provided. In one embodiment, an article comprises a particle, polymers, and intermolecular bonding groups. Each polymer comprises a first terminal end associated with the particle, a second terminal end associated with at least one intermolecular bonding group, and one or more repeat units. At least some of the intermolecular bonding groups do not comprise a moiety that is the same as a repeat unit or precursor thereof in the polymers.

In another embodiments, an article comprises a first component comprising a first particle, first polymers, and first intermolecular bonding groups and a second component comprising a second particle, second polymers, and second intermolecular bonding groups. Each first polymer is associated with the first particle and at least one first intermolecular bonding group. Each second polymer is associated with the second particle and at least one second intermolecular bonding group. At least a portion of the first intermolecular bonding groups are bonded to at least a portion of the second intermolecular bonding groups. At least some of the first intermolecular bonding groups do not comprise a moiety that is the same as a repeat unit or precursor thereof in the first polymers.

In another set of embodiments, methods are provided. In one embodiment, a method comprises applying a stimulus to a material in a first state thereby converting the material to a second state, wherein the first state is different than the second state. The material comprises a first component comprising a first particle, first polymers, and first intermolecular bonding groups and a second composition comprising a second particle, second polymers, and second intermolecular bonding groups. Each first polymer is associated with the first particle and at least one first intermolecular bonding group and each second polymer is associated with the second particle and at least one second intermolecular bonding group. At least some of the first intermolecular bonding groups do not comprise a moiety that is the same as a repeat unit or precursor thereof in the first polymers.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 7A shows a normalized UV-vis spectra of nanostructure dispersed in toluene according to certain embodiments;

FIG. 7B shows an UV-vis spectra of mixtures of complementary nanostructures, according to certain embodiments;

FIG. 7C shows, according to some embodiments, a graph of normalized extinction versus wavelength for a mixture of nanostructures undergoing multiple heat-cool cycles between 20 and 55° C. and the insets show optical images of a representative nanostructure mixture at the given temperatures, according to certain embodiments;

FIG. 17A shows the effect of 1,1,2,3 tetrachloroethane (TCE) on $T_M$ of nanostructures, according to some embodiments;

FIG. 17B shows the effect of TCE on $\Delta H_M$ of nanostructures, according to some embodiments;

FIG. 17C shows the effect of TCE on the enthalpy of melting of the small molecule diaminopyridine-thymine analogues, according to some embodiments;

FIG. 17D shows the cooperativity of nanostructures in different solvent mixtures of TCE, according to some embodiments.

DETAILED DESCRIPTION

Nanostructures and associated compositions, systems, and methods are provided. In some embodiments, a nanostructure may comprise polymers, intermolecular bonding groups, and a particle. The polymers may be associated with the particle and the intermolecular bonding groups may be associated with at least some of the polymers. In some embodiments, at least some of the intermolecular bonding groups may have a different chemical composition and/or chemical property (e.g., polarity) than the polymers. For instance, a certain repeat unit present in the polymers (e.g., nucleotide) may not be present in at least some of the intermolecular bonding groups. In some embodiments, nanostructures may reversibly associate with each other via the intermolecular bonding groups to form a material (e.g., nanoscale ordered material). In some such cases, the intermolecular bonding groups on different nanostructures may reversibly associate with each other, e.g., via a chemical or biological interaction. In some embodiments, the nanostructures may be designed, such that the energy required to disassociate at least a portion of the nanostructures in the material is greater than the energy required to dissociate a single association between intermolecular bonding groups. The nanostructures, described herein, may be used for a wide variety of applications including the formation of composite materials having beneficial chemical, mechanical, and/or physical properties.

Figure 1A:
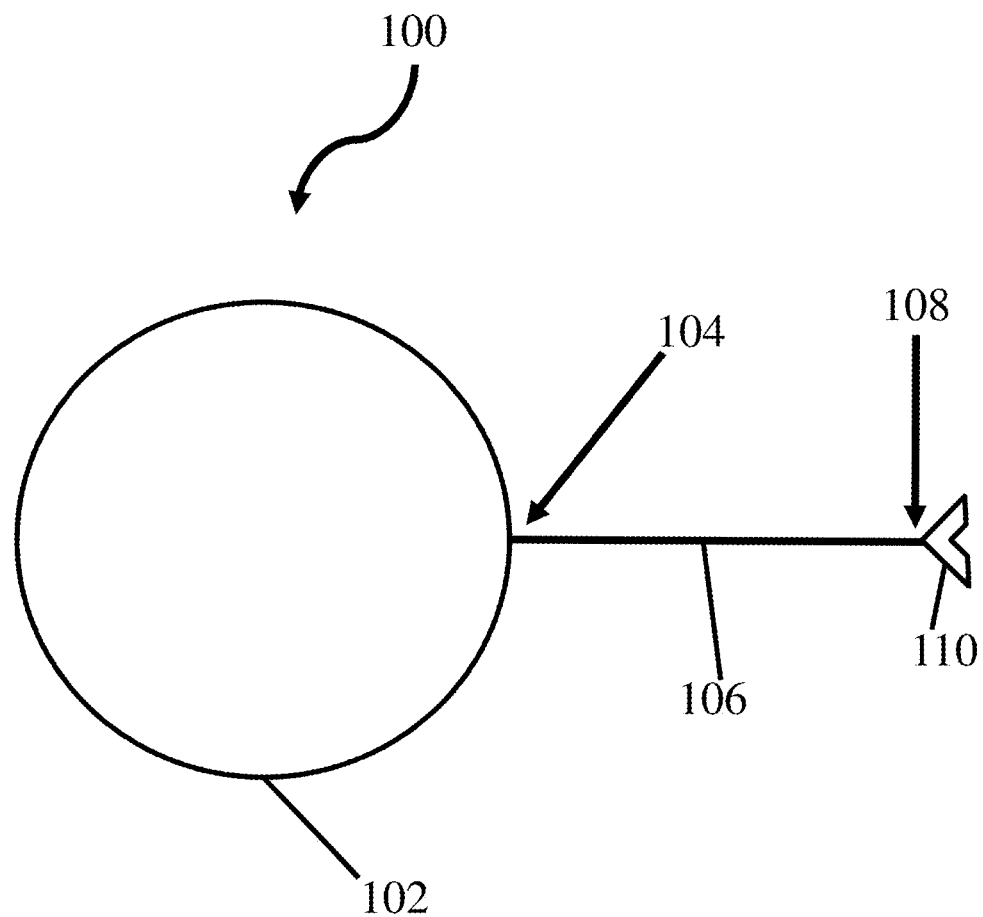
FIG. 1A shows a schematic of a nanostructure according to one set of embodiments.
Figure 1B:
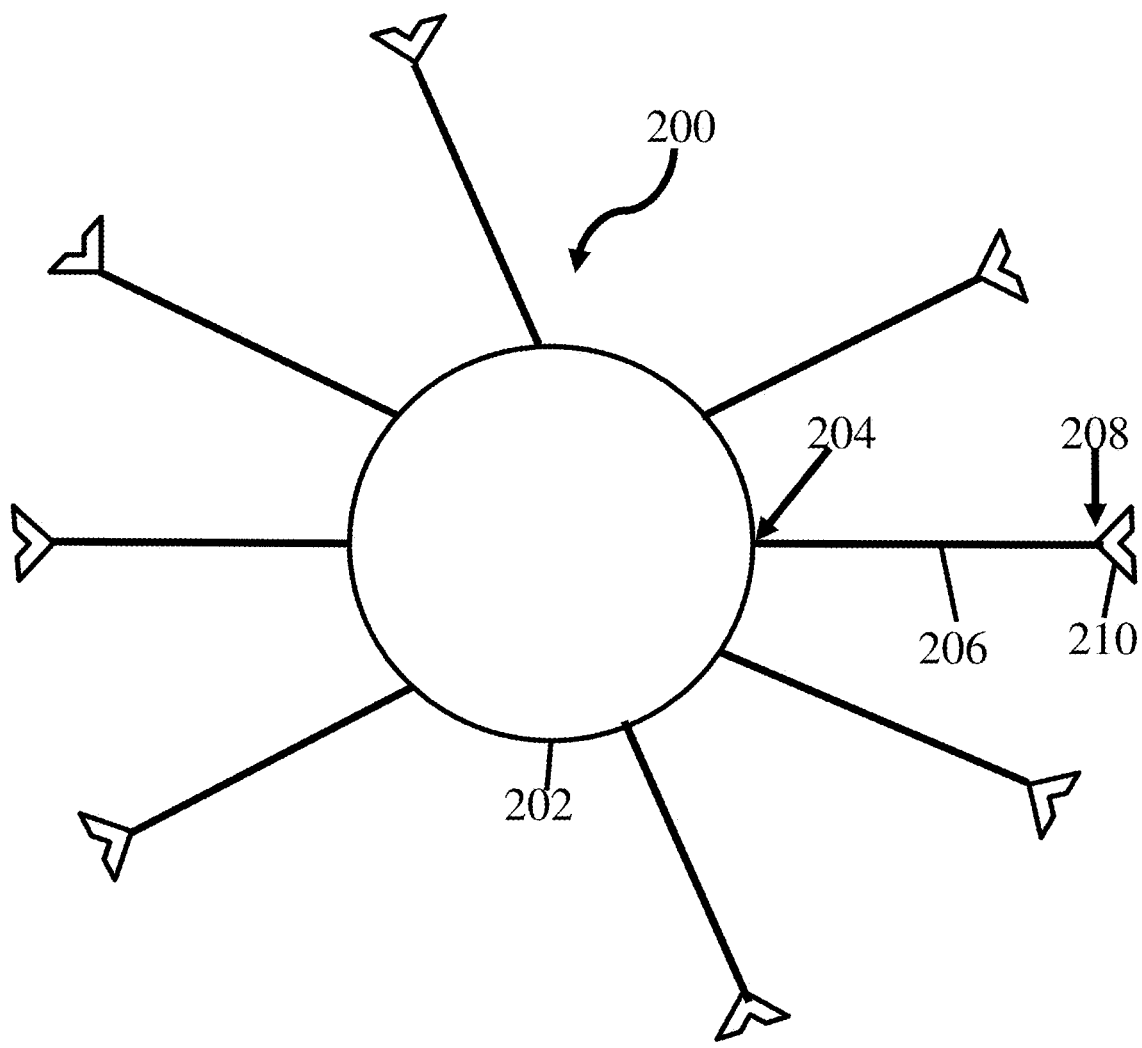
FIG. 1B shows a schematic of a nanostructure according to certain embodiments.
Figure 1C:
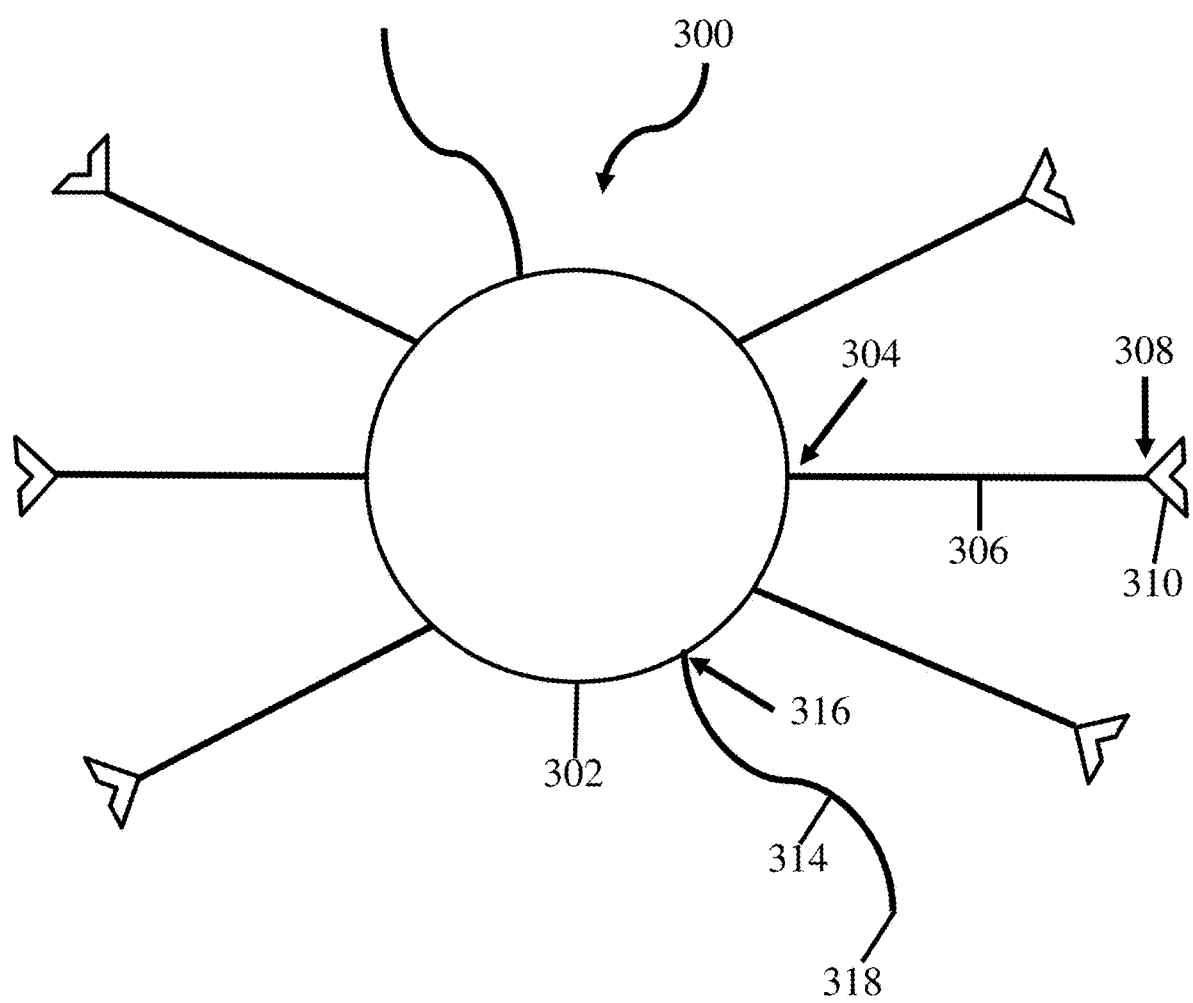
FIG. 1C shows a schematic of a nanostructure according to some embodiments.

Non-limiting examples of nanostructures are shown in FIGS. 1A-1C. In some embodiments, a nanostructure 100 may comprise a particle (e.g., nanoparticle). For instance, as illustrated in FIG. 1A, particle 102 may be associated (e.g., directly, indirectly) with a polymer 106. In some embodiments, the particle may be associated with the polymer via one or more chemical, biological, and/or physical interactions. In some instances, polymer 106 may be directly associated with the particle. For example, a terminal end of the polymer may be directly associated with the particle via a chemical bond (e.g., covalent bond) between a functional group on (e.g., on a surface of) and/or within (e.g., the interior of) the particle and a functional group on the terminal end 104 of the polymer. In certain instances, polymer 106 may be indirectly associated with the particle. In some such embodiments, the polymer may be associated with the particle via a linker (not shown). The linker may be associated with the particle and the polymer via one or more chemical, biological, and/or physical interactions. For example, the linker may be associated with the particle via one or more chemical bonds and/or the polymer via one or more chemical bonds. In some embodiments, the linker may comprise a functional group that forms a bond (e.g., covalent bond) with the particle and a second functional group that forms a bond with a functional group on the polymer (e.g., at the terminal end of the polymer). Non-limiting examples of suitable functional groups which can be used link the polymer and particle include ester, amide, amine, and anhydride, disulfide, triazole, silane, catechol, and carboxylic acid moieties.

As used herein, the term "terminal end" has its ordinary meaning in the art and may refer to an end group of a polymer. The end group of a polymer may be a group that is an extremity of the polymer and has only one point of attachment to the polymer.

Regardless of whether the polymer and particle are directly or indirectly associated with one another, the association between the particle and a portion of the polymer (e.g., terminal end) may have a relatively high bond strength (e.g., greater than or equal to about 100 kJ/mol), as described in more detail below. As used herein, the terms "bond strength", "association strength", "strength of an association" have their ordinary meaning in the art and may refer to the amount of energy released when components (e.g., molecules, polymer, particle, intermolecular bonding group, moiety) associate with one another. For example, if the association between two intermolecular boding groups results in a relatively large release of energy, then the association has a relatively high bond strength and/or the association is relatively strong. Conversely, if the association between two intermolecular boding groups results in a relatively small release of energy, then the association has a relatively low bond strength and/or the association is relatively weak. In general, the bond strength can be measured with any instrumental technique that correlates bond formation with a physical or chemical change in the structure, such as NMR, UV-Vis spectroscopy, IR spectroscopy, isothermal calorimetry, dynamic light scattering, x-ray diffraction, or other techniques. Unless otherwise mentioned, bond strength may be determined using NMR.

In some embodiments, the polymer may be associated with one or more (e.g., one, two or more, three or more, four or more) intermolecular bonding groups. In certain embodiments, an intermolecular bonding group is a molecule that may be capable of undergoing a biological, chemical, and/or physical interaction (e.g., chemical and/or biological interaction) with a moiety (e.g., another intermolecular bonding group) in another molecule. The intermolecular bonding may be capable of undergoing a reversible biological and/or chemical physical interaction with another molecule that has a certain bond strength (e.g., greater than or equal to about 15 kJ/mol and less than or equal to about 100 kJ/mol). For instance, as illustrated in FIG. 1A, polymer 106 may be associated (e.g., directly, indirectly) with an intermolecular bonding group 110. In some embodiments, the polymer may be associated with the intermolecular bonding group via one or more chemical, biological, and/or physical interactions.

In some instances, intermolecular bonding group 110 may be directly associated with the polymer. For example, a terminal end of the polymer may be directly associated with the intermolecular bonding group via a chemical bond (e.g., covalent bond) between a functional group in the intermolecular bonding group and a functional group on the terminal end of the polymer. In certain instances, polymer 106 may be indirectly associated with intermolecular bonding group 110. In some such embodiments, the polymer may be associated with the intermolecular bonding group via a linker (not shown). The linker may be associated with the intermolecular bonding group and the polymer via one or more chemical, biological, and/or physical interactions. For example, the linker may be associated with the intermolecular bonding group via one or more chemical bonds (e.g., covalent bonds) and/or the polymer via one or more chemical bonds (e.g., covalent bonds). In some such embodiments, the linker may be associated with a terminal end of the polymer via, e.g., a chemical bond (e.g., covalent bond) between a functional group in the linker and a functional group on the terminal end of the polymer.

Regardless of whether the polymer and intermolecular bonding group are directly or indirectly associated with one another, the association between the intermolecular bonding group and a portion of the polymer (e.g., terminal end) may have a relatively high bond strength (e.g., greater than or equal to about 100 kJ/mol), as described in more detail below. In some embodiments, the intermolecular bonding group may be a small molecule. In some such cases, the intermolecular bonding group may have a relatively small molecular weight (e.g., less than or equal to about 2,000 g/mol). Regardless of the type of intermolecular bonding group, the molecular weight of the intermolecular bonding group may be substantially less than the molecular weight of the polymer. For instance, the ratio of the molecular weight of polymer to the molecular weight of the intermolecular bonding group may be greater than or equal to about 1.5 (e.g., greater than or equal to about 2, greater than or equal to about 5, greater than or equal to about 10, greater than or equal to about 25, greater than or equal to about 50, greater than or equal to about 100). In some embodiments, the polymer may have high molecular weight relative to the intermolecular bonding group. For instance, the polymer may have a number-average molecular weight of greater than or equal to about 1,000 g/mol (e.g., greater than or equal to about 3,000 g/mol and less than or equal to about 250,000 g/mol).

In some embodiments, as illustrated in FIG. 1A, the polymer may associate with the particle and/or intermolecular bonding group at certain locations along the polymer. For instance, the association (e.g., direct, indirect) between the polymer and the particle may occur at terminal end 108 of polymer 106. In certain embodiments, the strength of the association between the polymer and other components of the nanostructure (e.g., intermolecular binding group, particle) may vary along the polymer. For instance, the association between the particle and terminal end 108 may have a relatively high bond strength (e.g., greater than or equal to about 100 kJ/mol). In some such embodiments, the strength of an association between the particle and one or more other portions of the polymer (e.g., backbone, repeat units, pendant groups) may be relatively weak. For instance, the bond strength of an association (e.g., any association) between the particle and one or more other portions of the polymer may be less than about 15 kJ/mol. In some cases, the particle may not associate with certain portions of the polymer (e.g., repeat units, pendant groups). In certain cases, the particle may only associate with a terminal end of the polymer. In certain embodiments, the association (e.g., direct, indirect) between the polymer and the intermolecular bonding group may occur at terminal end 108 of polymer 106. In some such cases, one terminal end of the polymer may be associated with the particle and the other terminal end (e.g., 104) of the polymer may be associated with one or more intermolecular bonding groups. The association between intermolecular binding group 110 and terminal end 108 may have a relatively high bond strength (e.g., greater than or equal to about 100 kJ/mol). In some such embodiments, the strength of an association between the intermolecular binding group and one or more other portions of the polymer (e.g., backbone, repeat units, pendant groups) may be relatively weak. For instance, the bond strength of an association (e.g., any association) between the intermolecular binding group and one or more other portions of the polymer may be less than about 15 kJ/mol. In some cases, the intermolecular binding group may not associate with certain portions of the polymer (e.g., repeat units, pendant groups). In certain cases, the intermolecular binding group may only associate with a terminal end of the polymer.

In some embodiments, the strength of an association (e.g., any association) between the particle and one or more (e.g., all) intermolecular bonding groups may be relatively weak. For instance, the bond strength of an association (e.g., any association) between particle 102 and intermolecular bonding group 110 may be less than about 15 kJ/mol. In certain embodiments, the particle may not associate with one or more (e.g., two or more, any) intermolecular bonding groups. In some embodiments in which the strength of an association (e.g., any association) between particle 102 and intermolecular interaction group 110 is weak, the intermolecular interacting group may be oriented away from the particle, as illustrated in FIG. 1A. In embodiments in which intermolecular interacting group 110 is associated with terminal end 108, terminal end 108 may be oriented away from the particle.

In some such embodiments, the intermolecular bonding group may comprise one or more moiety that is different from at least a portion of the polymer (e.g., repeat units, pendant groups). In certain embodiments, intermolecular bonding group 110 may have a different chemical composition and/or chemical property (e.g., polarity) than at least a portion (e.g., backbone of the polymer, repeat units, pendant groups) of polymer 106. For instance, the intermolecular bonding group may not comprise a moiety (e.g., chemical structure) that is a precursor of or similar to (e.g., substantially the same as) a repeat unit and/or pendant group in the polymer. In some such cases, the polymer may comprise a repeat unit (e.g., synthetic repeat unit, nucleotide, saccharide, amino acid, lipid) and the intermolecular bonding group may not comprise a chemical structure that is a precursor of and/or similar to (e.g., substantially the same as) the repeat unit. For example, the polymer may comprise a nucleotide as a repeat unit and the intermolecular bonding group may not comprise the same nucleotide and/or may not comprise any nucleotide. As another example, the polymer may comprise a synthetic repeat unit and the intermolecular bonding group may not comprise a chemical structure that is a precursor of (e.g., monomer from which the repeat unit is derived) and/or similar to (e.g., substantially the same as) the synthetic repeat unit.

As used herein, the term "precursor," has its ordinary meaning in the art and may refer to a chemical structure which, after undergoing loss and/or gain of a ligand, functional group, or the like, and/or undergoing a reaction (e.g., chemical reaction of a functional group), dissociation from a compound, agent, mixture, etc., results in the chemical structure of interest. For instance, a monomer may be a precursor of a repeat unit. As another example, an amino acid may be a precursor of an amino acid residue. Conversely, an amino acid residue may be a precursor of an amino acid.

In certain embodiments, the intermolecular bonding group may comprise different types of moieties than the polymer. In some such embodiments, the intermolecular bonding group may not comprise the same type of moieties (e.g., polar moieties, nucleotide, saccharide, amino acid) as the polymer. For instance, the polymer may comprise non-polar repeat units and/or pendant groups and the intermolecular bonding group may not comprise a non-polar moiety. That is, the intermolecular bonding group may comprise (e.g., consist essentially of) polar moieties. In some such cases, the polymer may be non-polar and the intermolecular bonding group may be polar. In other instances, the polymer may comprise polar repeat units and/or pendant groups and the intermolecular bonding group may not comprise a polar moiety. That is, the intermolecular bonding group may comprise (e.g., consist essentially of) non-polar moieties. In some such cases, the polymer may be polar and the intermolecular bonding group may be non-polar. As another example, the polymer may comprise a naturally occurring moiety or derivative thereof (e.g., nucleotide, saccharide, amino acid, lipid), e.g., as a repeat unit and the intermolecular bonding group may not comprise a naturally occurring moiety or derivative thereof. That is, the intermolecular bonding group may comprise (e.g., consist essentially of) non-naturally occurring moieties. In other instances, the polymer may comprise a non-naturally occurring moiety, e.g., as a repeat unit and the intermolecular bonding group may not comprise non-naturally occurring moieties. That is, the intermolecular bonding group may comprise (e.g., consist essentially of) non-naturally occurring moieties. As yet another example, the polymer may be non-polar and the intermolecular bonding group may be polar. In other instances, the polymer may comprise polar repeat units and/or pendant groups and the intermolecular bonding group may not comprise a polar moiety. That is, the intermolecular bonding group may comprise (e.g., consist essentially of) non-polar moieties. In some such cases, the intermolecular bonding group may comprise a hydrogen bonding acceptor, a hydrogen bonding donor, an electron acceptor, an electron donor, a dynamic covalent bond acceptor, a dynamic covalent bond donor, a pi-pi stacking acceptor, a pi-pi stacking donor, a metal coordination acceptor, a metal coordination donor, a host (e.g., moiety comprising a cavity that can accommodate a guest moiety, cyclodextrin, metallacrowns, crown ethers), and/or a guest (e.g., a moiety capable of occupying a cavity, cleft, or pocket within the molecular structure of a host moiety) moiety. The polymer may not comprise such moieties.

Accordingly, in some embodiments, at least a portion (e.g., one or more repeat units, all repeat units, substantially all) of the polymer may be different than at least a portion of the intermolecular bonding group (e.g., one or more moieties in, substantially all). In certain embodiments, at least a portion of the polymer may have a different chemical composition and/or chemical property than at least a portion of the intermolecular bonding group, as described above. In one example the intermolecular bonding group may comprise a moiety having a molecular weight of greater than or equal to about 100 g/mol that is not present in a repeat unit of the polymer, pendant group of polymer, and/or the entire polymer. In some cases, the polymer may not comprise a moiety that is the same as at least a portion (e.g., a moiety having a molecular weight of greater than or equal to about 100 g/mol) of the intermolecular bonding group. For example, the polymer may not comprise a moiety that is the same as any moiety in the intermolecular bonding group that has a molecular weight of greater than or equal to about 100 g/mol (e.g., greater than or equal to about 150 g/mol).

As described herein, in some embodiments, a nanostructure may comprise a plurality of polymers associated with a particle (e.g., nanoparticle). For instance, as illustrated in FIG. 1B, a nanostructure 200 comprising particle 202 may be associated (e.g., directly, indirectly) with polymers 206. The polymers may be associated with the particles as described above with respect to FIG. 1A. For instance, a terminal end of at least some (e.g., each) of the polymers may be directly or indirectly associated with the particle (e.g., a surface of the particle) via, e.g., a chemical bond (e.g., covalent bond) or linker, respectively. For example, each polymer 206 may comprise a first terminal end 204 and a second terminal end 208 as illustrated in FIG. 1B. First terminal ends 204 may be associated with particle 202. In some embodiments, the strength of the association between polymers 206 and other components of the nanostructure (e.g., intermolecular binding group, particle) may vary along the polymer as described above with respect to FIG. 1A. For example, the association between particle 202 and terminal end 204 may be relatively strong (e.g., bond strength of greater than or equal to about 100 kJ/mol) while the strength of an association (e.g., any association) between the particle and one or more other portions of polymers 206 (e.g., repeat units, pendant groups) may be relatively weak (e.g., bond strength of less than about 15 kJ/mol).

In some embodiments, at least some (e.g., all) of polymers 206 may have a substantially similar or the same chemical composition. In certain embodiments, at least some (e.g., all) of polymers 206 may have a different chemical composition than another polymer. In some embodiments, the polymers may cover a significant portion of the surface area of the polymer. For instance, in some embodiments, the grafting density of the polymers on the particle is greater than or equal to about 0.15 polymer/nm 2 (e.g., and less than or equal to about 1.00 polymer/nm$^2$). Without being bound by theory, it is believed that the grafting density of the polymers on the particle, and according the grafting density of the intermolecular bonding groups, may influence the number of associations formed between adjacent nanostructures in a material and the energy required to disrupt at least a portion of the associations in a material, as described in more detail below.

In some embodiments, as illustrated in FIG. 1B, polymers 206 may be associated (e.g., directly, indirectly) with one or more (e.g., one, two or more, three or more, four or more) intermolecular bonding groups 210. The intermolecular bonding groups may be associated with the polymers as described above with respect to FIG. 1A. For instance, a terminal end of at least some (e.g., each) of the polymers may be directly or indirectly associated with one or more intermolecular bonding group via, e.g., a chemical bond (e.g., covalent bond) or linker, respectively. For example, each polymer 206 may comprise a second terminal end 208 that is associated with intermolecular bonding group 210 as illustrated in FIG. 1B. In certain embodiments, at least some (e.g., all) of intermolecular bonding groups 210 are only associated with polymers 206 at the second terminal end. In some embodiments, the strength of the association between polymers 206 and intermolecular binding groups 210 may vary along the polymer as described above with respect to FIG. 1A. For example, the association between intermolecular bonding groups 210 and terminal ends 208 may be relatively strong (e.g., bond strength of greater than or equal to about 100 kJ/mol) while the strength of an association (e.g., any association) between the intermolecular bonding groups and one or more other portions of polymers 206 (e.g., repeat units, pendant groups) may be relatively weak (e.g., bond strength of less than about 15 kJ/mol). In some embodiments, at least some of intermolecular bonding groups 210, and accordingly second terminal ends 208, may be oriented away from particle 202 as illustrated in FIG. 1B. In certain cases, at least some of intermolecular bonding groups 210, and accordingly second terminal ends 208, may be oriented toward from particle 202.

In some embodiments, at least some (e.g., all) of intermolecular bonding groups 210 may have a substantially similar or the same chemical composition. In certain embodiments, at least some (e.g., all) of intermolecular bonding groups 210 may have a different chemical composition than another intermolecular bonding group. In some embodiments, intermolecular bonding groups 210 may comprise one or more moiety that is different from at least a portion of the polymers (e.g., repeat units, pendant groups) 206 as described above with respect to FIG. 1A. For instance, in certain embodiments, at least some (e.g., all) of intermolecular bonding groups 210 may have a different chemical composition and/or chemical property (e.g., polarity) than at least a portion (e.g., backbone of the polymer, repeat units, pendant groups) of polymers 206 as described above with respect to FIG. 1A. For example, at least some of the intermolecular bonding groups may not comprise a moiety (e.g., chemical structure) that is a precursor of or similar to (e.g., substantially the same as) a repeat unit and/or pendant group in one or more (e.g., at least some, all) of polymers 206. In certain embodiments, at least some (e.g., all) of intermolecular bonding groups may comprise different types of moieties than at least some (e.g., all) of polymers as described above with respect to FIG. 1A. For example, at least some of the intermolecular bonding groups are polar and at least some of the polymers are non-polar. In some such cases, at least some (e.g., all) of the intermolecular bonding groups comprise a polar moiety. As another example, at least some of the intermolecular bonding groups are non-polar and at least some of the polymers are polar. In some such cases, at least some (e.g., all) of the intermolecular bonding groups comprise a non-polar moiety. In certain embodiments, at least some of the polymers do not comprise a moiety that is similar to and/or substantially the same as at least some of (e.g., any of) the intermolecular bonding groups or precursors thereof and/or one or more moieties within the intermolecular bonding groups as described above with respect to FIG. 1A. For example, at least some (e.g., all) of the intermolecular bonding groups may comprise a biological moiety (e.g., nucleotide) and at least some of the polymers do not comprise the biological moiety (e.g., nucleotide), e.g., as repeat unit and/or pendant group.

In some embodiments, the strength of the association between any two polymers 206 may be relatively weak (e.g., bond strength of less than about 15 kJ/mol). In certain embodiments, at least some (e.g., all) of polymers 206 may not be associated with another polymer 206 via, e.g., a chemical or biological interaction.

In some embodiments, as illustrated in FIG. 1C, a nanostructure 300 may comprise one or more non-bonding polymers 314 that are not associated (e.g., directly, indirectly) with any intermolecular bonding groups 310. For example, non-bonding polymers 314 may comprise a first terminal end 316 that is associated with particle 302 and a second terminal end 318 that is not associated with any intermolecular group. In some embodiments, nanostructure may also comprise polymers 306 that are associated (e.g., directly, indirectly) with one or more (e.g., one, two or more, three or more, four or more) intermolecular bonding groups 310 as described above with respect to FIGS. 1A and 1B.

Without being bound by theory, it is believed that the grafting density of the polymers associated with one or more intermolecular bonding groups, and according the grafting density of the intermolecular bonding groups, may controlled, at least in part, by modifying the ratio of non-bonding polymers to polymers associated with one or more intermolecular bonding groups associated with the particle.

In some embodiments, the strength of the association between non-bonding polymers 314 and particle 302 may vary along the polymer as described above with respect to FIG. 1A. For example, the association between particle 302 and first terminal ends 316 may be relatively strong (e.g., bond strength of greater than or equal to about 100 kJ/mol) while the strength of an association (e.g., any association) between the particle and one or more other portions of polymers 314 (e.g., second terminal end, repeat units, pendant groups) may be relatively weak (e.g., bond strength of less than about 15 kJ/mol). For example, the strength of an association (e.g., any association) between the particle 302 and second terminal ends 318 of the non-bonding polymers may be relatively weak (e.g., bond strength of less than about 15 kJ/mol). In some such embodiments, at least some (e.g., all) of second terminals 318, may be oriented away from particle 302 as illustrated in FIG. 1C. In certain embodiments, the non-bonding polymers may only be associated with the particle via first terminal ends 316.

In some embodiments, the strength of the association between at least some (e.g., all) non-bonding polymers 314 and at least some (e.g., all) intermolecular binding groups 310 may be relatively weak (e.g., bond strength of less than about 15 kJ/mol). In certain embodiments, at least some (e.g., all of) of non-bonding polymers 314 may not be associated with any intermolecular bonding group. In some embodiments, the strength of the association between at least some (e.g., all) non-bonding polymers 314 and at least some (e.g., all) polymers 206 may be relatively weak (e.g., bond strength of less than about 15 kJ/mol). In certain embodiments, at least some (e.g., all of) of non-bonding polymers 314 may not be associated with any polymers. In some embodiments, the strength of the association between any two non-bonding polymers 314 may be relatively weak (e.g., bond strength of less than about 15 kJ/mol). In certain embodiments, at least some (e.g., all of) of non-bonding polymers 314 may not be associated with another non-bonding polymer 314 via, e.g., a chemical or biological interaction.

Figure 2A:
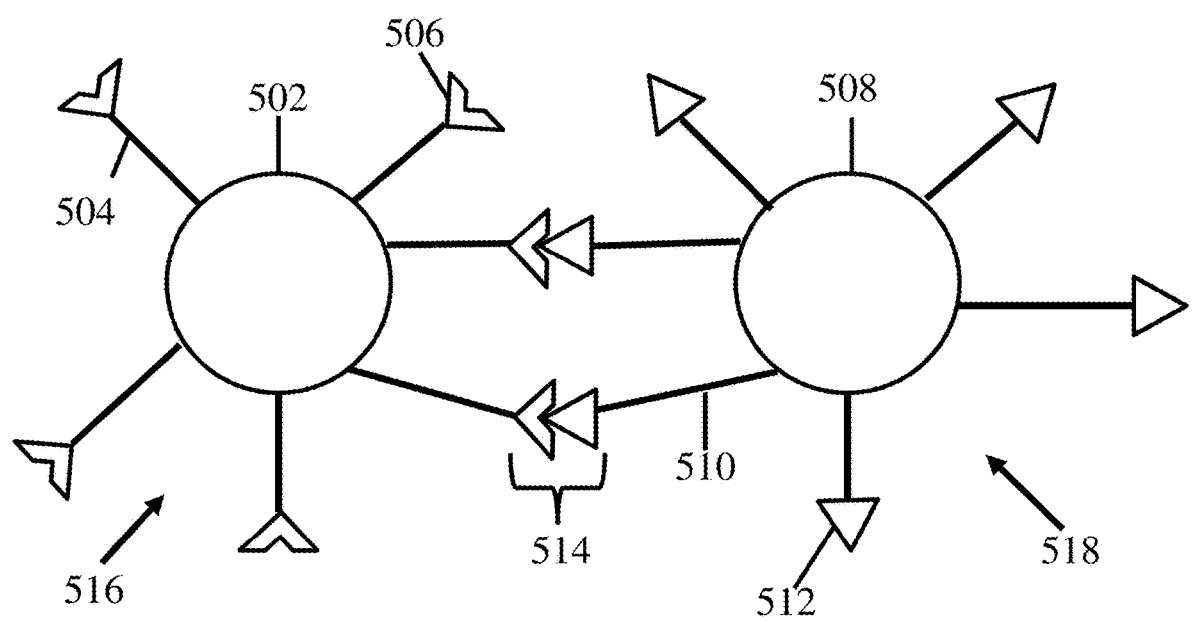
FIG. 2A shows a schematic of two nanostructures associated with each other, according to one set of embodiments.

As noted above, in some embodiments, two or more nanostructures may be associated (e.g., reversibly, irreversibly) with each other via intermolecular bonding groups. For instance, as illustrated in FIG. 2A, first nanostructure 516 may be associated with second nanostructure 518 via associations 514. First nanostructure 516 may comprise a first particle 502, first polymers 504, and first intermolecular bonding groups 506. First nanostructure 516 may be arranged as described with respect to FIGS. 1A, 1B, and/or 1C and elsewhere herein. Second nanostructure 518 may comprise a second particle 508, second polymers 510, and second intermolecular bonding groups 512. Second nanostructure 518 may be arranged as described with respect to FIGS. 1A, 1B, and/or 1C and elsewhere herein. In certain embodiments, the first nanostructure and/or the second nanostructure may optionally comprise non-bonding polymers that lack an association with any intermolecular bonding group, e.g., as described with respect to FIG. 1C. In some embodiments, the first nanostructure may be different than the second nanostructure. In other embodiments, the first nanostructure may be the same as the second nanostructure.

In some embodiments, at least some of first intermolecular bonding groups 506 are capable of forming an association with at least some of the second intermolecular bonding groups 512. In some such embodiments, at least some of the first intermolecular bonding groups may be complementary to at least some of second intermolecular bonding groups 512 via associations 514. In certain embodiments, at least some of the first intermolecular bonding groups may be associated with at least some of second intermolecular bonding groups 512 via associations 514. In general, a first intermolecular bonding group may be associated with a second intermolecular bonding group via any suitable chemical, biological, and/or physical interactions. In some instances, a first intermolecular bonding group may be associated with a second intermolecular bonding group via any a chemical (e.g., non-covalent bond) or a biological interaction. For example, a first intermolecular bonding group may be associated with a second intermolecular bonding group via a chemical interaction, such as a chemical bond. The chemical bond may be a dynamic covalent bond or a non-covalent bond. In some cases, the chemical bond is a non-covalent bond such as a hydrogen bond, ionic bond, dative bond, and/or a Van der Waals interaction. As another example, a first intermolecular bonding group may be associated with a second intermolecular bonding group via a biological interaction. In some such embodiments, an association between a first intermolecular bonding group and a second intermolecular bonding group may occur via a biological binding event (i.e., between complementary pairs of biological molecules). In some embodiments, at least some (e.g., all) of the associations may a chemical composition that is similar to and/or substantially the same as another association. In certain embodiments, at least some (e.g., all) of the associations may a chemical composition that is different than another association. In some embodiments, at least some (e.g., all) of the associations may be the same type (e.g., chemical interaction, non-covalent bond, biological interaction) as another association. In certain embodiments, at least some (e.g., all) of the associations may be different than another association.

In some embodiments, complementary intermolecular bonding groups may comprise one or more (e.g., two or more, three or more) complementary functional groups or other moiety (e.g., hydrogen bond donor/acceptor, electron donor/acceptor, dynamic covalent acceptor/donor, pi-pi stacking acceptor/donor, metal coordination acceptor/donor, host/guest). Complementary moieties (e.g., functional groups) will be known to those of ordinary skill in the art. The association between complementary intermolecular bonding groups may be based on a biological or chemical interaction as described herein. For example, the association between complementary intermolecular bonding groups may be based on the formation of one or more bonds, such as an ionic bond, a hydrogen bond (e.g., between hydroxyl, amine, carboxyl, thiol, and/or similar functional groups), a dative bond (e.g., complexation or chelation between metal ions and monodentate or multidentate ligands), Van der Waals interactions, or the like. In certain embodiments in which a chemical bond is formed, the intermolecular bonding group may be selected such that it comprises at least one or more (e.g., two or more, three or more, four or more) hydroxyl functional groups, at least one or more (e.g., two or more, three or more, four or more) carboxylic acid ester functional groups, at least one or more (e.g., two or more, three or more, four or more) nitrogen containing base functional group, at least one or more (e.g., two or more, three or more, four or more) aryl (e.g., phenyl) functional groups, a plurality of carboxyl functional group, at least one or more (e.g., two or more, three or more, four or more) tertiary amide functional groups, or combinations thereof. As a non-limiting example, if an intermolecular bonding group comprises an aryl group, a complementary functional group on a complementary intermolecular bonding group may be selected to be an aryl functional group, such that pi-interactions can occur between the surface of the substrate and the small organic molecule. As another example, if an intermolecular bonding group comprises a hydrogen-bond donating group, a complementary functional group on a complementary intermolecular bonding group may be selected to be a hydrogen-bond accepting group. As yet another example, if an intermolecular bonding group comprises a carboxylic acid group, a complementary functional group in a complementary intermolecular bonding group may comprise a tertiary amide group. In one example, if an intermolecular bonding group comprises a carbonyl group, a complementary functional group in a complementary intermolecular bonding group a hydroxyl group. As yet another specific example, both complementary intermolecular bonding groups may comprise phenyl groups, and the association may be a pi-stacking interaction.

As noted above, in some embodiments, the first intermolecular bonding groups may preferentially associate with the second intermolecular bonding group. That is, in some embodiments, the strength of the association between the first intermolecular bonding group and the second intermolecular bonding group may be greater than at least some other possible associations between components of the first and second nanostructures. For example, the strength of the association between the first intermolecular bonding group and the second intermolecular bonding group may be greater than any other possible associations between components of the first and second nanostructures, except the associations between the polymer and the particle and the polymer and the one or more intermolecular bonding group. Without being bound by theory, it is believed that the preferential association between the intermolecular bonding groups allows the associations between the nanostructures to be controlled in a predictable manner by, e.g., the application of a stimulus (e.g., energy, condition) as described in more detail below. Moreover, the preferential association between the first intermolecular bonding group and the second intermolecular bonding group may prevent the formation of other associations between the nanostructures (e.g., association between solvent and intermolecular bonding group, association between non-terminal end of polymer and intermolecular bonding group, association between particle and intermolecular bonding group) that may lead to aggregation that may not be predictably controlled.

In some embodiments, the bond strength of the association between at least a portion of the first polymer (e.g., backbone, repeat unit, pendant group) and the first intermolecular bonding group is less than the bond strength between the first intermolecular bonding group and the second intermolecular group. In certain embodiments, the bond strength of an association between at least a portion of the second polymer (e.g., backbone, repeat unit, pendant group) and the second intermolecular bonding group is less than the bond strength between the first intermolecular bonding group and the second intermolecular group. In some embodiments, the bond strength of an association between at least a portion of the second polymer (e.g., backbone, repeat unit, pendant group) and the first intermolecular bonding group is less than the bond strength between the first intermolecular bonding group and the second intermolecular group. In certain embodiments, the bond strength between at least a portion of the first polymer (e.g., backbone, repeat unit, pendant group) and the second intermolecular bonding group is less than the bond strength between the first intermolecular bonding group and the second intermolecular group.

In certain embodiments, the strength of an association between at least some (e.g., all) of the first intermolecular bonding groups and at least some (e.g., all) of second intermolecular bonding groups may be less than the strength of the association between the first terminal end of the first and/or second polymer and the particle. In some instances, the strength of an association between at least some (e.g., all) of the first intermolecular bonding groups and at least some (e.g., all) of second intermolecular bonding groups may be less than the strength of the association between the second terminal end of the first and/or second polymer and the first and/or second polymer, respectively.

Figure 2B:
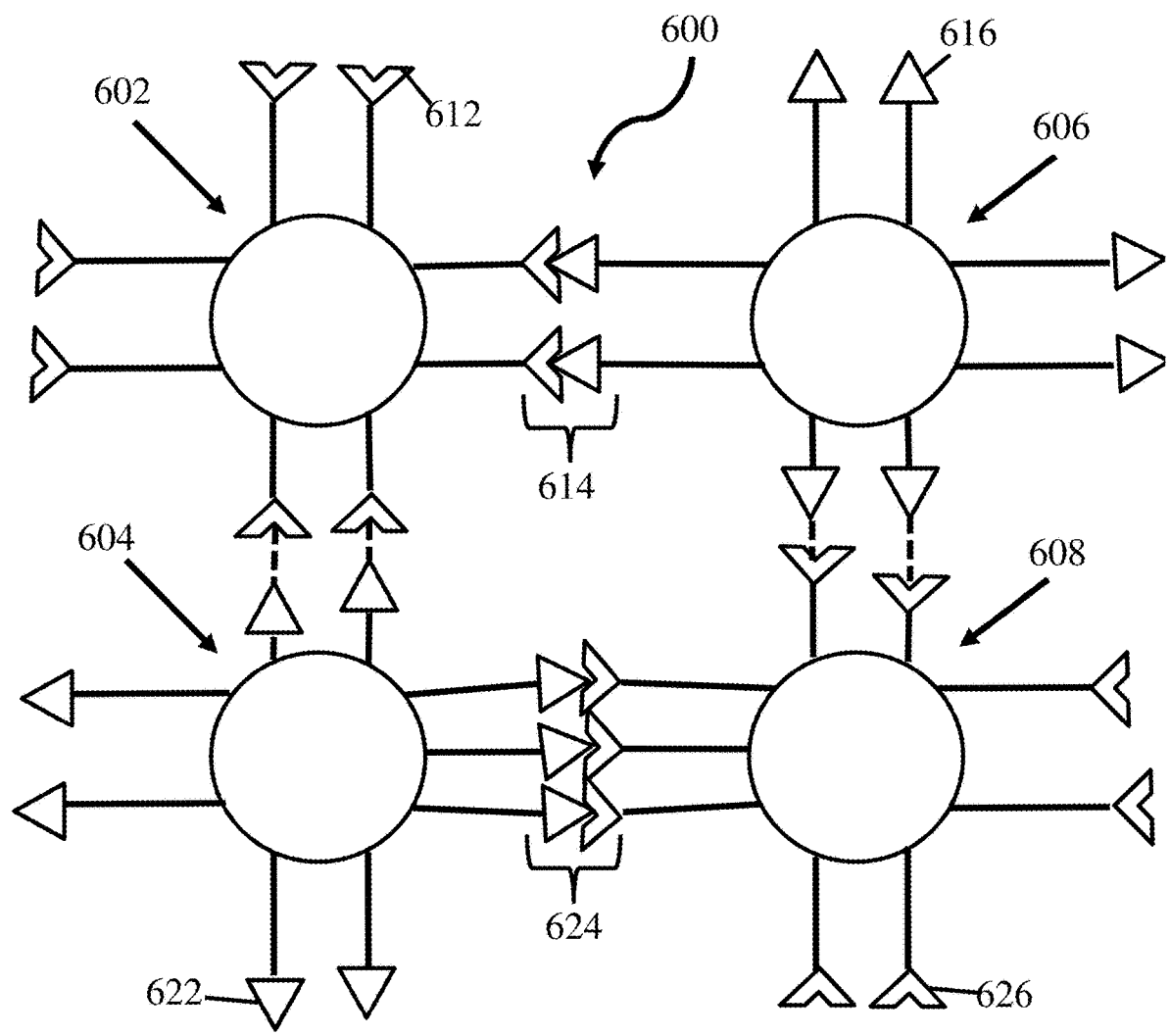
FIG. 2B shows a schematic of two nanostructures associated with each other, according to certain embodiments.

As described herein, in some embodiments, nanostructures may associate with each other via the intermolecular bonding groups to form a material (e.g., nanoscale ordered material). In some embodiments, as illustrated in FIG. 2B, intermolecular bonding groups 612, 616, 622, and 626 on different nanostructures 602, 604, 606, and 608 may associate with each other, e.g., via a chemical bond or biological interaction (e.g., 614, 624) to form a material 600. In some embodiments, the strength of the association between the intermolecular bonding groups may be selected such that the association between at least some (e.g., all) of the nanostructures are reversible. The collective bond strength of associations is greater than the bond strength of a single association between two intermolecular bonding group. As used herein, the term "collective bond strength" has its ordinary meaning in the art and may refer to the energy released upon the formation of multiple associations between components (e.g., intermolecular bonding groups) The collective bond strength may be measured using thermal melt experiments in which the fraction of associated components is measured as a function of temperature. In some such embodiments, the energy required to disassociate at least a portion of the nanostructures in the material is greater than the energy required to dissociate a single association between intermolecular bonding groups. The inventors have surprisingly discovered that when a nanostructure is associated with another nanostructure via two or more (e.g., two, three or more, four or more, six or more, eight or more) associations having a certain bond strength (e.g., greater than or equal to about 20 kJ/mol and less than or equal to about 100 kJ/mol), the nanostructures may be dissociated via application of a stimulus and the collective bond strength of the association is greater than the bond strength of a single association.

In some embodiments, nanostructures may associate with one another to an ordered or disordered material. In some embodiments, nanostructures may associate with one another to form a ordered material (e.g., material with nanoscale ordering). As used herein, the term "ordered material" has its ordinary meaning in the art and may refer to a material having translational symmetry and/or that displays higher order peaks in a graph produced from a scattering technique, such as X-ray scattering. For example, an ordered material may have a regular two-dimensional and/or three-dimensional arrangement of particles, polymers, and/or intermolecular bonding groups. In some embodiments, an ordered material may have a regular interparticle distance, a regular crystalline or non-crystalline arrangement, and/or lack the presence of certain defects (e.g. grain boundaries, vacancies). As used herein, the term "disordered material" has its ordinary meaning in the art and may refer to a material that does not have translational symmetry and/or displays higher order peaks in a graph produced from a scattering technique, such as X-ray scattering. In some embodiments, at least some (e.g., all) of the nanostructures may be different than other nanostructures. For instance, the material may comprise at least two different types of nanostructures. In other embodiments, the material may comprise (e.g., consist essentially of) nanostructures that have the same chemical composition.

As described herein, in some embodiments, a material comprising the nanostructures, described herein, may be converted from a first state (e.g., disordered material) to a second state (e.g., ordered material) via the application of one or more stimuli. In certain embodiments, the material may be stimuli-responsive, such that the arrangement of the nanostructures in the material may change (e.g., reversibly) upon exposure to certain conditions. For instance, upon exposure to heat at or above the melting temperature of at least one nanostructure (e.g., two or more nanostructures, all nanostructures), the material may be converted from a first state to a second state having a different property (e.g., degree of nanoscale order, chemical property, mechanical property, physical property) than the first state. For example, the material may be converted from a disordered state to an ordered state. In certain embodiments, exposure to another set of conditions may cause the material to be converted from the second state to the first state. For example, the material may be converted from a ordered state to a disordered state upon exposure to temperatures at or below the melting temperature of at least one nanostructure (e.g., two or more nanostructures, all nanostructures).

Figure 3:
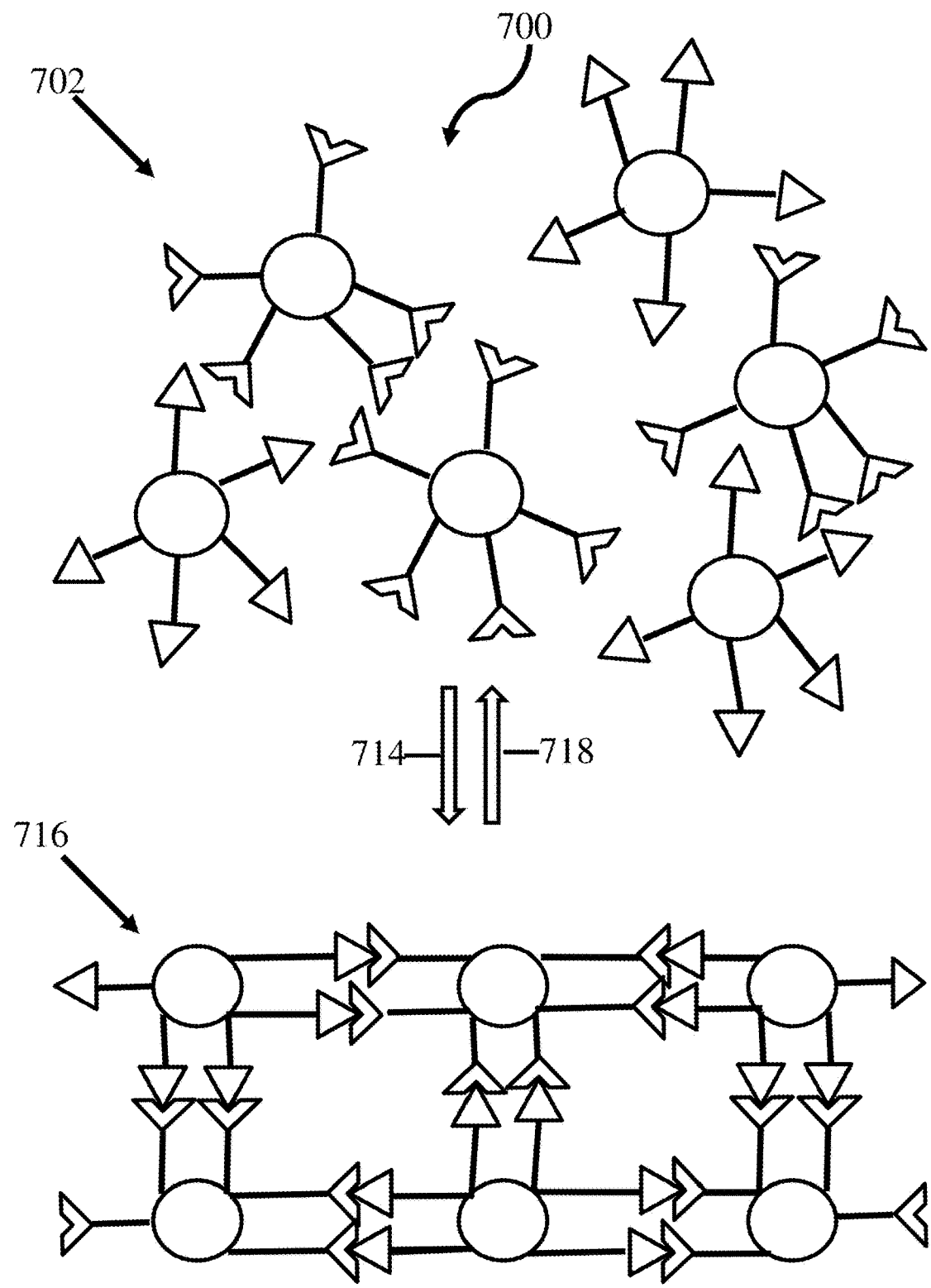
FIG. 3 shows a schematic of the application of stimulus to a first state of a material, according to certain embodiments.

A non-limiting example of conversion of a material from a first state (e.g., disordered state) to a second state (e.g., ordered state) is shown in FIG. 3. In some embodiments, a material 700 may be stimuli responsive, such that a property of the material reversibly changes under certain conditions. For instance, the material may have a first arrangement of nanostructures 702 under a first set of conditions, as illustrated in FIG. 3, and exposure to a second set of conditions (e.g., application of energy, exposure to certain chemical compounds, concentration of certain chemical compounds), as indicated by arrow 714 may result in the material having a second arrangement of nanostructures 716 as illustrated in FIG. 3. The application of one or more stimuli may reversibly alter a property of the material (e.g., crystalline structure, non-crystalline structure, order, presence of defects). For example, exposure to a third set of conditions, as indicated by arrow 718, may produce the first arrangement of nanostructures, again. In certain embodiments, the second arrangement of nanostructures may be stable upon exposure to the first set of conditions again. In some such embodiments, the third set of conditions and the first set of conditions may be different. In other embodiments, the second arrangement of nanostructures may be unstable upon exposure to the first set of conditions again. In some such embodiments, the third set of conditions and the first set of conditions may be similar and/or substantially the same.

Without being bound by theory, it is believed that the complementary intermolecular bonding groups rearrange upon exposure to certain conditions to obtain the most energetically favorable positions. It is believed that, in some instances, an ordered material allows for the maximum number of associations between nanostructures to form. Accordingly, it is believed that when nanostructures are placed under conditions that allow certain associations to disassociate and re-associate, the material will approach thermodynamic equilibrium in which the number of association is maximized. The material may be configured to provide sufficient flexibility to the intermolecular bonding groups to allow for reorganization of the associations between the nanostructures, as described herein.

In some embodiments, the nanostructures may be converted from a first state to a second state in a solvent. In some such embodiments, the solvent is compatible with one or more stimuli used in the conversion process. For example, in embodiments in which the stimulus is thermal energy, the freezing point of the solvent may be less than the melting point of at least some (e.g., each) of the nanostructures in the material and/or the boiling point of the solvent may be greater than the melting point of at least some (e.g., each) of the nanostructures in the material. In some embodiments, the first intermolecular bonding groups may preferentially associate with the second intermolecular bonding group within the solvent. That is, in some embodiments, the strength of the association between the first intermolecular bonding group and the second intermolecular bonding group may be greater than any possible associations between components of the nanostructures and the solvent. For example, the strength of the association between the solvent and one or more intermolecular bonding groups (e.g., first intermolecular groups, second intermolecular bonding groups, any intermolecular bonding groups) may be less than the strength of the association between complementary intermolecular bonding groups. In other embodiments, the nanostructures may be converted from a first state to a second state in the absence of a solvent.

As used herein, a "set of conditions" or "conditions" may comprise, for example, a particular solvent, chemical compound (e.g., ionic compound), temperature, pH, electromagnetic radiation, electrical state, mechanical force, or combinations thereof. Some conditions may involve the application of energy (e.g., mechanical, electrical, chemical).

As described herein, a nanostructure may comprise a particle (e.g. a nanoparticle). As used herein, the term "particle" refers to a small object, fragment, or piece of material and includes, without limitation, microparticles and nanoparticles. Particles may be composed of a single substance or multiple substances. In certain embodiments, the particles are substantially solid throughout and/or comprise a core that is substantially solid throughout. In some embodiments, a particle may not include a micelle, a liposome, or an emulsion. The term "microparticle" refers to a particle having a characteristic dimension of less than about 1 millimeter and greater than or equal to about 1 micron, where the characteristic dimension of the particle is the smallest cross-sectional dimension of the particle. The term "nanoparticle" refers to a particle having a characteristic dimension of less than or equal to about 1 micron (e.g., and greater than or equal to about 1 nanometer), where the characteristic dimension of the particle is the smallest cross-sectional dimension of the particle. In some embodiments, a nanoparticle may have a characteristic maximum cross-sectional dimension of less than or equal to about 1 micron. A "maximum cross-sectional dimension" of a particle, as used herein, refers to the largest dimension between two points on opposed outer boundaries of the particle, as measured perpendicular to the length of the particle (e.g., the length of a nanoparticle). A "smallest cross-sectional dimension" of a particle, as used herein, refers to the smallest dimension between two points on opposed outer boundaries of the particle, as measured perpendicular to the length of the particle (e.g., the length of a nanoparticle). In some embodiments, the particle may be spherical or nonspherical.

A particle may have any suitable size. In some embodiments, a particle has at least one cross-sectional dimension (at least two cross-sectional dimensions, smallest cross-sectional dimension, maximum cross-sectional dimension) that is/are greater than or equal to about 1 nm and less than or equal to about 1 micron (e.g., between 2 nm and 500 nm, or between 2 nm and 250 nm). In some embodiments, a nanoparticle has at least one cross-sectional dimension (or at least two cross-sectional dimensions) that is/are less than or equal to about 1 micron, less than or equal to about 500 nm, less than or equal to about 250 nm, less than or equal to about 100 nm, less than or equal to about 75 nm, less than or equal to about nm, less than or equal to about 40 nm, less than or equal to about 30 nm, less than or equal to about 20 nm, less than or equal to about 10 nm, or less than or equal to about 5 nm. In certain embodiments, the nanoparticle has at least one cross-sectional dimension (or at least two cross-sectional dimensions) that is/are greater than or equal to about 1 nm, greater than or equal to about 2 nm, greater than or equal to about 5 nm, greater than or equal to about 10 nm, greater than or equal to about 50 nm, greater than or equal to about 100 nm, greater than or equal to about 250 nm, or greater than or equal to about 500 nm. Combinations of the above-noted ranges are also possible. In some cases, the above-noted cross-sectional dimension is a maximum cross-sectional dimension.

A particle can be formed of any suitable material. In some embodiments, the particle comprises a metal. Non-limiting examples of metals include Au, Ag, Cd, Cr, Co, Ti, Zn, Cu, Pb, Mn, Ni, Mg, Fe, Pd, and/or Pt. In other embodiments, a particle comprises a semiconductor (e.g., Rh, Ge, silicon, silicon compounds and alloys, cadmium selenide, cadmium sulfide, indium arsenide, and indium phosphide). In some cases, the particle may comprise a Group II-VI (e.g., IV-VI) element. In certain embodiments, the particle comprises a metal oxide or a metal fluoride. In some embodiments, the particle may comprise an oxide (e.g., $SiO_2$). In certain embodiments, the particle may comprise Ag, CdSe, PbS, $Fe_3O_4$, Si, or $BaTiO_3$.

In some cases, the particle a comprises an alloy. In some cases, the particle a comprises a doped compound. Combinations of such and other materials are also possible. The particle may be electronically and/or thermally conductive in some embodiments, or non-electronically and/or non-thermally conductive in other embodiments.

In other embodiments, a particle formed by the methods described herein may be an organic particle. In some cases, a particle may comprise a polymer, which may be cross-linked or non-crosslinked. The polymer may be, for example, a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen. Conductive polymers may be used in some embodiments.

It should be understood that, in certain embodiments, the particle may be composed of other materials besides synthetic polymers and natural polymers (e.g., polysaccharides, carbohydrates, polypeptides). In certain embodiments, a ceramic such as calcium phosphate ceramic is used. Exemplary calcium phosphate ceramics include tricalcium phosphate, hydroxyapatite, and biphasic calcium phosphate.

In general, the particle may have any suitable shape. In some cases, the particle may be a sphere, cube, rod, plate, or the like. Other shapes are also possible, e.g., needle, ribbon, filament, tube, cone or the like. In some aspects, the shape and/or size of the particle may influence the overall shape of the material and/or arrangement of the nanostructures within the material.

In general, the particle may have any suitable chemical and/or physical properties. In certain embodiments, the particle may have certain optical properties. For instance, the particles may absorb and/or emit electromagnetic radiation in the visible, ultraviolet, and/or UV-visible range. In some cases, the particle may exhibit fluorescence or luminescence. In certain cases, the particle is detectable by UV-visible spectroscopy, surface plasmonic resonance, fluorescence, luminescence, or dynamic light scattering. In certain embodiments, the particle may have certain magnetic properties. In certain embodiments, the particle may be a magnetic nanoparticle. According to certain embodiments, the particle may be diamagnetic, paramagnetic, ferromagnetic, antiferromagnetic, ferrimagnetic, or antiferromagnetic. In some aspects, the particle is detectable by magnetic susceptibility, magnetic resonance imaging, and/or electron paramagnetic resonance. In some embodiments, the particle may have certain thermoelectric properties. For example, changing the temperature of a particle may create an electric potential, and/or changing the electric potential of a particle may result in a temperature difference. In some embodiments, the particle may be detectable by four-point probe measurements of electrical properties, measurements of electrical conductivity, and measurements of thermal conductivity. In some embodiments, the particle may be porous. In other embodiments, the particles may be non-porous.

As described herein, the nanostructure may comprise one or more polymers associated with a particle. In general, in suitable polymer may be used. Polymers are generally extended molecular structures comprising backbones which optionally contain pendant side groups, wherein the term backbone is given its ordinary meaning as used in the art, e.g., a linear chain of atoms within the polymer molecule by which other chains may be regarded as being pendant. Typically, but not always, the backbone is the longest chain of atoms within the polymer. A polymer may be a copolymer, for example, a block, alternating, or random copolymer. Polymers may be obtained from natural sources or be created synthetically. A polymer may also comprise a mixture of polymers. In some embodiments, the polymer may be acyclic or cyclic. Polymer molecules may be obtained from natural sources or be created synthetically.

An exemplary, non-limiting list of polymers includes polysaccharides (e.g., alginate); polynucleotides; polypeptides; peptide nucleic acids; polyurethane; polyamides; polycarbonates; polyanhydrides; polydioxanone; polyacetylenes and polydiacetylenes; polyphosphazenes; polysiloxanes; polyolefins; polyamines; polyesters; polyethers; poly(ether ketones); poly(alkaline oxides); poly(ethylene terephthalate); poly(methyl methacrylate); polystyrene; poly (lactic acid)/polylactide; poly(glycolic acid); poly(lactic-co-glycolic acid); poly(caprolactone); polysaccharides such as starch; poly(orthoesters); poly(anhydrides); poly(ether esters) such as polydioxanone; poly(carbonates); poly (amino carbonates); and poly(hydroxyalkanoates) such as poly(3-hydroxybutyrate) and poly(3-hydroxybutyrate-co-3-hydroxyvalerate) and derivatives and block, random, radial, linear, or teleblock copolymers, cross-linkable materials such as proteinaceous materials and/or blends of the above. Also suitable are polymer molecules formed from monomeric alkylacrylates, alkylmethacrylates, alpha-methylstyrene, vinyl chloride and other halogen-containing monomers, maleic anhydride, acrylic acid, acrylonitrile, and the like. Monomers can be used alone, or mixtures of different monomers can be used to form homopolymers and copolymers. Other potentially suitable polymer molecules are described in the Polymer Handbook, Fourth Ed. Brandrup, J. Immergut, E. H., Grulke, E. A., Eds., Wiley-Interscience: 2003, which is incorporated herein by reference in its entirety. In some embodiments, polymer molecules may be biodegradable. In other embodiments, a polymer may be non-degradable.

As described herein, the one or more polymers have certain physical properties. For example, the one or more polymers can be rigid or flexible (or non-rigid). As used herein, a "rigid" portion of a polymer refers to a portion wherein the spatial relationship (e.g., angle, distance, etc.) between adjacent monomeric moieties cannot change, outside of normal molecule-scale changes in temperature, etc., without breaking at least one bond. For example, a portion of a polymer including $sp^3$-hybridized carbon atoms may not be rigid (e.g., alkyl chains, heteroalkyl chains, and the like), while $sp^2$-hybridized or sp-hybridized carbon atoms may impart a higher degree of rigidity (e.g., aryl groups, alkynyl groups). However, portions of a polymer including $sp^3$-hybridized carbon atoms, wherein the $sp^3$-hybridized carbon atoms, for example, form bridgeheads between fused rings in a bicyclic or polycyclic structure or otherwise form a shape-persistent moiety may be considered to form a rigid structure. In some embodiments, a polymer or portion thereof may comprise a metal atom, wherein the metal atom, when bound to or otherwise attached to the polymer, imparts a degree of rigidity to the polymer.

In general, the polymers may have any suitable molecular weight. For example, in some embodiments, the number average molecular weight of one or more polymers may be greater than or equal to about 1,000 g/mol, greater than or equal to about 3,000 g/mol, greater than or equal to about 5,000 g/mol, greater than or equal to about 10,000 g/mol, greater than or equal to about 25,000 g/mol, greater than or equal to about 50,000 g/mol, greater than or equal to about 75,000 g/mol, greater than or equal to about 100,000 g/mol, greater than or equal to about 125,000 g/mol, or greater than or equal to about 150,000 g/mol, greater than or equal to about 175,000 g/mol, greater than or equal to about 200,000 g/mol, or greater than or equal to about 225,000 g/mol. In some instances, the number average molecular weight of one or more polymers may be less than or equal to about 250,000 g/mol, less than or equal to about 225,000 g/mol, less than or equal to about 200,000 g/mol, less than or equal to about 175,000 g/mol, less than or equal to about 150,000 g/mol, less than or equal to about 125,000 g/mol, less than or equal to about 100,000 g/mol, or less than or equal to about 75,000 g/mol, less than or equal to about 50,000 g/mol, less than or equal to about 25,000 g/mol, less than or equal to about 10,000 g/mol, or less than or equal to about 5,000 g/mol. Combinations of the above-referenced ranges are also possible (e.g., greater than or equal to about 1,000 g/mol and less than or equal to about 250,000 g/mol, greater than or equal to about 3,000 g/mol and less than or equal to about 250,000 g/mol). The number average molecular weight may be determined using gel permeation chromatography (GPC), NMR, laser light scattering, intrinsic viscosity, vapor pressure osmometry, small angle neutron scattering, laser desorption ionization mass spectrometry, matrix assisted laser desorption ionization mass spectrometry (MALDI MS), or electrospray mass spectrometry or may be obtained from a manufacturer's specifications. Unless otherwise indicated the values of number average molecular weight described herein are determined by gel permeation chromatography (GPC).

In some embodiments, polymers have any suitable number of repeat units. For instance, the one or more polymers having greater than or equal to about 10, greater than or equal to about 20, greater than or equal to about 50, greater than or equal to about 100, greater than or equal to about 200, greater than or equal to about 300, or greater than or equal to about 400. In some instances, the number of repeat units may be less than or equal to about 500, less than or equal to about 400, less than or equal to about 300, less than or equal to about 200, less than or equal to about 100, or less than or equal to about 50. Combinations of the above-referenced ranges are also possible (e.g., greater than or equal to about 10 and less than or equal to about 500). Other values of the number of repeat units in the first component are also possible. The number of repeat units may be determined using gel permeation chromatography (GPC), NMR, or may be obtained from a manufacturer's specifications.

In some embodiments, the polydispersity index (weight average molecular weight/number average molecular weight) of the polymers in a nanostructure may be relatively small. For instance, in some embodiments, the polydispersity index of the polymers in a nanostructure may be less than or equal to about 4.0, less than or equal to about 3.6, less than or equal to about 3.3, less than or equal to about 3.0, less than or equal to about 2.8, less than or equal to about 2.6, less than or equal to about 2.4, less than or equal to about 2.2, less than or equal to about 2.0, less than or equal to about 1.8, less than or equal to about 1.6, less than or equal to about 1.4, less than or equal to about 1.2, or less than or equal to about 1.0. In some instances, the polydispersity index of a polymer composition may be greater than or equal to about 1.0, greater than or equal to about 1.2, greater than or equal to about 1.4, greater than or equal to about 1.6, greater than or equal to about 1.8, greater than or equal to about 2.0, greater than or equal to about 2.2, greater than or equal to about 2.4, greater than or equal to about 2.6, greater than or equal to about 2.8, greater than or equal to about 3.0, greater than or equal to about 3.3, greater than or equal to about 3.6, or greater than or equal to about 4.0. It should be understood that all combinations of the above-referenced ranges are possible (e.g. greater than or equal to about 1.1 and less than or equal to about 2.6, greater than or equal to about 1.4 and less than or equal to about 3.5). Other values of polydispersity index are also possible.

In some embodiments, the one or more polymers (e.g., all polymers, polymers associated with one or more intermolecular bonding groups) may have any suitable grafting density. For example, the grafting density of the one or more polymers may be less than or equal to about 1.15 polymer/$nm^2$, less than or equal to about 1.05 polymer/$nm^2$, less than or equal to about 0.95 polymer/$nm^2$, less than or equal to about 0.85 polymer/$nm^2$, less than or equal to about 0.75 polymer/$nm^2$, less than or equal to about 0.65 polymer/$nm^2$, less than or equal to about 0.55 polymer/$nm^2$, less than or equal to about 0.45 polymer/$nm^2$, less than or equal to about 0.35 polymer/$nm^2$, less than or equal to about 0.25 polymer/$nm^2$, or less than or equal to about 0.15 polymer/$nm^2$. In some instances, the grafting density of the one or more polymers may greater than or equal to about 0.15 polymer/$nm^2$, greater than or equal to about 0.25 polymer/$nm^2$, greater than or equal to about 0.35 polymer/nm², greater than or equal to about 0.45 polymer/nm², greater than or equal to about 0.55 polymer/nm², greater than or equal to about 0.65 polymer/nm², greater than or equal to about 0.75 polymer/nm², greater than or equal to about 0.85 polymer/nm², greater than or equal to about 0.95 polymer/nm², or greater than or equal to about 1.05 polymer/nm². It should be understood that all combinations of the above-referenced ranges are possible (e.g. greater than or equal to about 0.15 polymer/nm 2 and less than or equal to about 1.00 polymer/nm², greater than or equal to about 0.45 polymer/nm 2 and less than or equal to about 0.65 polymer/nm²). Other values of grafting density are also possible.

In general a polymer (e.g., all polymers, polymers associated with one or more intermolecular bonding groups, non-bonding polymers) may have any suitable length. In some embodiments, the length of the particle may influence the interparticle distance in the material. For example, the one or more polymers may have a length of less than or equal to about 5.0 microns, less than or equal to about 4.0 microns, less than or equal to about 3.0 microns, less than or equal to about 2.0 microns, or less than or equal to about 1.0 microns. In some embodiments, the length of the one or more polymers may be greater than or equal to about 1.0 microns, greater than or equal to about 2.0 microns, greater than or equal to about 3.0 microns, or greater than or equal to about 4.0 microns. It should be understood that all combinations of the above-referenced ranges are possible (e.g. greater than or equal to about 2.0 microns and less than or equal to about 4.0 microns, greater than or equal to about 1.0 microns and less than or equal to about 2.0 microns). Other values of grafting density are also possible.

As described herein, at least some polymers may be associated with one or more intermolecular bonding groups. Any suitable intermolecular bonding group may be used. For instance, in some embodiments, the intermolecular bonding group may be a small molecule (e.g., synthetic moiety, nucleotide, amino acid, saccharide). In some embodiments, the intermolecular bonding group may be a biological polymer (e.g., antibody, antibody fragment, oligonucleotide).

As used herein, the term "small molecule" refers to pharmaceutically active agent, whether naturally-occurring or artificially created (e.g., via chemical synthesis) that has a relatively low molecular weight. In some embodiments, t small molecule is an organic compound (i.e., it contains carbon). For instance, the small molecule may contain multiple carbon-carbon bonds, stereocenters, and other functional groups (e.g., amines, hydroxyl, acyls, and heterocyclic rings, etc.). For example, the small molecule may be diaminopyridinge (DAP) or thymine (Thy). In certain embodiments, the small molecule is an inorganic compound. In certain embodiments, the molecular weight of a small molecule is at most about 2,500 g/mol, is at most about 2,000 g/mol, at most about 1,500 g/mol, at most about 1,250 g/mol, at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 2,500 g/mol, at least about 200 g/mol and at most about 2,000 g/mol, at least about 200 g/mol and at most about 1,500 g/mol) are also possible. In general, the small molecules described herein have a molecular weight smaller than the particles described herein.

The intermolecular bonding groups may have any suitable molecular weight. For example, the molecular weight of the intermolecular bonding group is at most about 2,500 g/mol, at most about 2,000 g/mol, at most about 1,500 g/mol, at most about 1,250 g/mol, at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of the intermolecular bonding group is at least about 50 g/mol, at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 50 g/mol and at most about 2,500 g/mol, at least about 100 g/mol and at most about 2,000 g/mol, at least about 100 g/mol and at most about 1,500 g/mol) are also possible. In general, the intermolecular bonding groups described herein have a molecular weight smaller than the polymers described herein.

In some embodiments, the intermolecular bonding group may comprise a hydrogen bond acceptor moiety, a hydrogen bond donor moiety, an electron acceptor moiety, an electron donor moiety, a host for accepting a coordination ligand, a guest for donating a coordination ligand, a metal coordination acceptor, a metal coordination donor, dynamic covalent bond donor, dynamic covalent bond acceptor, ionic bond donor, ionic bond acceptor, dative bond donor, dative bond acceptor, Van der Waals interaction donor, Van der Waals interaction acceptor, or the like.

In some embodiments, the intermolecular bonding groups are associated with a substrate. For example, a portion of the intermolecular bonding groups may be associated with the surface of a substrate. In some embodiments, the substrate may comprise metal, glass, silicon, etc. In some such embodiments, the nanostructures may be used as coating on a substrate.

According to some embodiments, the association between one or more intermolecular bonding groups with a substrate may have any suitable bond strength. For example, the bond strength of the association between one or more intermolecular bonding groups and a substrate may be less than or equal to about 30 kJ/mol, less than or equal to about 25 kJ/mol, less than or equal to about 20 kJ/mol, less than or equal to about 15 kJ/mol, less than or equal to about 10 kJ/mol, or less than or equal to about 5 kJ/mol. In some instances, the association between one or more intermolecular bonding group and a substrate may have a bond strength of greater than or equal to about 5 kJ/mol, greater than or equal to about 10 kJ/mol, greater than or equal to about 15 kJ/mol, greater than or equal to about 20 kJ/mol, or greater than or equal to about 25 kJ/mol. All combinations of the above-referenced ranges are possible (e.g., greater than or equal to about 10 kJ/mol and less than or equal to about 20 kJ/mol).

"Association" between two or more components would be understood by those of ordinary skill in the art based on this description. As noted above, one or more polymers may be associated with one or more intermolecular bonding groups and/or one or more polymers may be associated with a particle. The association between polymers and the intermolecular binding groups and/or the polymers and the particle can be of any suitable type. For example, the association between the polymers and the intermolecular binding groups and/or the polymers and the particle can comprise a chemical interaction, such as a covalent bond. As used herein, an irreversible association has its ordinary meaning in the art. For example, an irreversible association may occur when an association cannot be disassociated (e.g., broken) without cleavage of a non-dynamic covalent bond in one more of the associated components (e.g., nanostructure, intermolecular bonding group). As another example, an irreversible association may occur when an association cannot be disassociated (e.g., broken) and re-associated under similar conditions under which the association was formed.

As described herein, intermolecular bonding groups may be associated with each other. The association between intermolecular bonding groups can be of any association that has a suitable binding strength. For example, the association between complementary intermolecular binding groups may comprise a chemical interaction, a physical interaction, and/or a biological interaction In some embodiments, two or more intermolecular binding groups (e.g., complementary intermolecular binding groups) may associate via a chemical interaction, such as a chemical bond. The chemical bond may be a covalent bond or non-covalent bond. In some cases, the chemical bond is a non-covalent bond such as a hydrogen bond, ionic bond, dative bond, and/or a Van der Waals interaction. One or more of the intermolecular binding groups may comprise functional groups capable of forming such bonds. For example, an intermolecular binding group may include at least one hydrogen atom capable of interacting with a pair of electrons on a hydrogen-bond acceptor of another components (e.g., a photosensitive material) to form the hydrogen bond. In some embodiments, the intermolecular binding group may include an electron-rich or electron-poor moiety, such that it may form an electrostatic interaction with another of the intermolecular binding groups. It should be understood that covalent and non-covalent bonds between components may be formed by any type of reactions, as known to those of ordinary skill in the art, using the appropriate functional groups to undergo such reactions. Chemical interactions suitable for use with various embodiments described herein can be selected readily by those of ordinary skill in the art, based upon the description herein.

In some embodiments, an association between two or more intermolecular binding groups (e.g., complementary intermolecular binding groups) may occur via a biological binding event (i.e., between complementary pairs of biological molecules). For example, a component (e.g., a harmonic generation material, a photosensitive material, and/or an agent) may include an entity such as biotin that specifically binds to a complementary entity, such as avidin or streptavidin, on another component (e.g., a harmonic generation material, a photosensitive material, and/or an agent). Other examples of biological molecules that may form biological bonds between pairs of biological molecules include, but are not limited to, proteins, nucleic acids, glycoproteins, carbohydrates, hormones, and the like. Specific examples include, but are not limited to, an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Biological interactions between the harmonic generation material and the photosensitive material (and/or between these components and an agent) suitable for use in the embodiments described herein can be selected readily, by those of ordinary skill in the art, based upon the description herein as their function, examples of such biological interactions, and knowledge herein and in the art as to simple techniques for identifying suitable chemical interactions.

The association between complementary intermolecular bonding groups have any suitable bond strength. The interactions between nanostructures may have any suitable bond strength. For instance, in some embodiments, the association between intermolecular bonding groups may have a bond strength of greater than or equal to about 15 kJ/mol, greater than or equal to about 20 kJ/mol, greater than or equal to about 30 kJ/mol, greater than or equal to about 40 kJ/mol, greater than or equal to about 50 kJ/mol, greater than or equal to about 60 kJ/mol, greater than or equal to about 70 kJ/mol, greater than or equal to about 80 kJ/mol, or greater than or equal to about 90 kJ/mol. In some instances, bond strength may be less than or equal to about less than or equal to about 100 kJ/mol, less than or equal to about kJ/mol, less than or equal to about 80 kJ/mol, less than or equal to about 70 kJ/mol, less than or equal to about 60 kJ/mol, less than or equal to about 50 kJ/mol, less than or equal to about 40 kJ/mol, less than or equal to about 30 kJ/mol, or less than or equal to about 20 kJ/mol. All combinations of the above-referenced are also possible (e.g., greater than or equal to about 15 kJ/mol and less than or equal to about 100 kJ/mol, greater than or equal to about 20 kJ/mol and less than or equal to about 100 kJ/mol).

As described herein, nanostructures may be used to form a material. In some embodiments, the material may be a composite material. In some embodiments, the material may have beneficial chemical, mechanical, electrical, optical, magnetic, biological, or physical properties or combinations thereof.

In some embodiments, a method may comprise converting a material comprising nanostructures, as described herein, from a first state to a second state. In some such embodiments, the conversion process may take place in a solvent. In some embodiments, the particle, polymers, and intermolecular bonding groups may have a similar solubility and/or the same solubility in the solvent. Without being bound by theory, it is believed that the significant differences in solubility between the particle, polymers, and intermolecular bonding groups in the solvent used for the method may inhibit and/or prevent reorganization of one or more components of the nanostructures (e.g., particle, polymers, and intermolecular bonding groups) and/or the nanostructures. As used herein, "solubility" refers to the ability of a substance to be carried in the solvent without precipitating out. The solubility may be expressed in terms of concentration of the saturated solution of the molecule at standard conditions.

Any suitable solvent may be used. In some embodiments, the solvent is an organic solvent. Non-limiting examples of suitable solvent include, N,N'-dimethylformamide, tetrahydrofuran, acetone, chloroform, toluene, 1,1,2,2,-tetrachloroethane, water, monomers of polymers (e.g. styrene), molten polymers (e.g., polymers above their respective glass transition temperatures) or combinations thereof.

Certain aspects are related to methods where a stimulus is applied to a material in a first state, as discussed herein. In some embodiments, applying a stimulus may comprise applying energy (e.g., thermal annealing, heat, electric field, mechanical force) to the material. In certain embodiments, applying a stimulus may comprise exposing the material to a certain set of conditions.

Various times of exposure to stimulus may be used. In some embodiments, exposure to a stimulus is applied for about at least 1 minute, about at least 2 minutes, about at least 5 minutes, about at least 10 minutes, about at least 20 minutes, about at least 30 minutes, about at least 45 minutes, or about at least 60 minutes. In some embodiments, exposure to a stimulus is applied for less than about 60 minutes, less than about 45 minutes, less than about 30 minutes, less than about 20 minutes, less than about 10 minutes, less than about 5 minutes, less than about 2 minutes, or less than about 1 minute. In addition, combinations of any of these are also possible; for example, the exposure to a stimuli is applied for 2 minutes to 5 minutes U.S. Provisional Patent Application Ser. No. 62/397,684, filed Sep. 21, 2016, and entitled "Self-Assembling Nanocomposite Tectons," is incorporated herein by reference in its entirety for all purposes.

The following examples are intended to illustrate certain embodiments of the present invention, but do not exemplify the full scope of the invention.

Example 1

This example describes an exemplary nanostructure (i.e. nanocomposite tecton) and formation of a material using the nanostructure.

Figure 4:
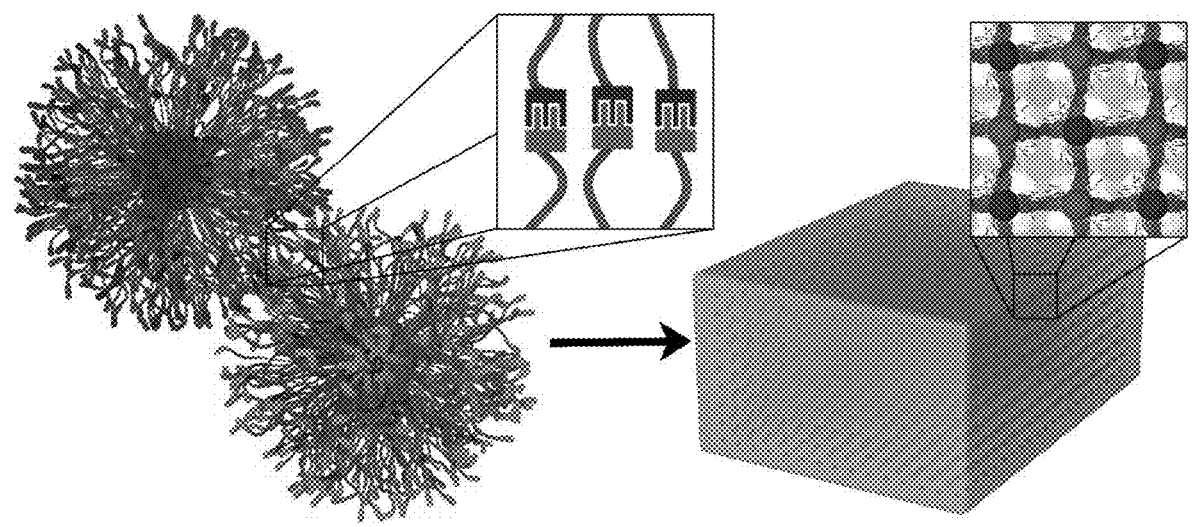
FIG. 4 show, according to some embodiments, a schematic of nanostructures and a material comprising nanostructures.
Figure 5:
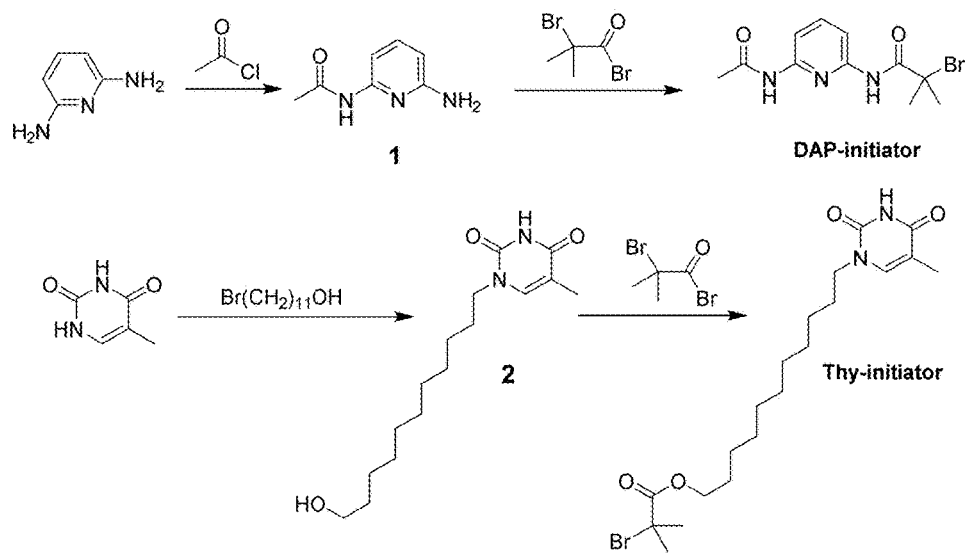
FIG. 5 shows, according to some embodiments, a synthetic route to a diaminopyridine-derivative and a thymine-derivative.
Figure 6:
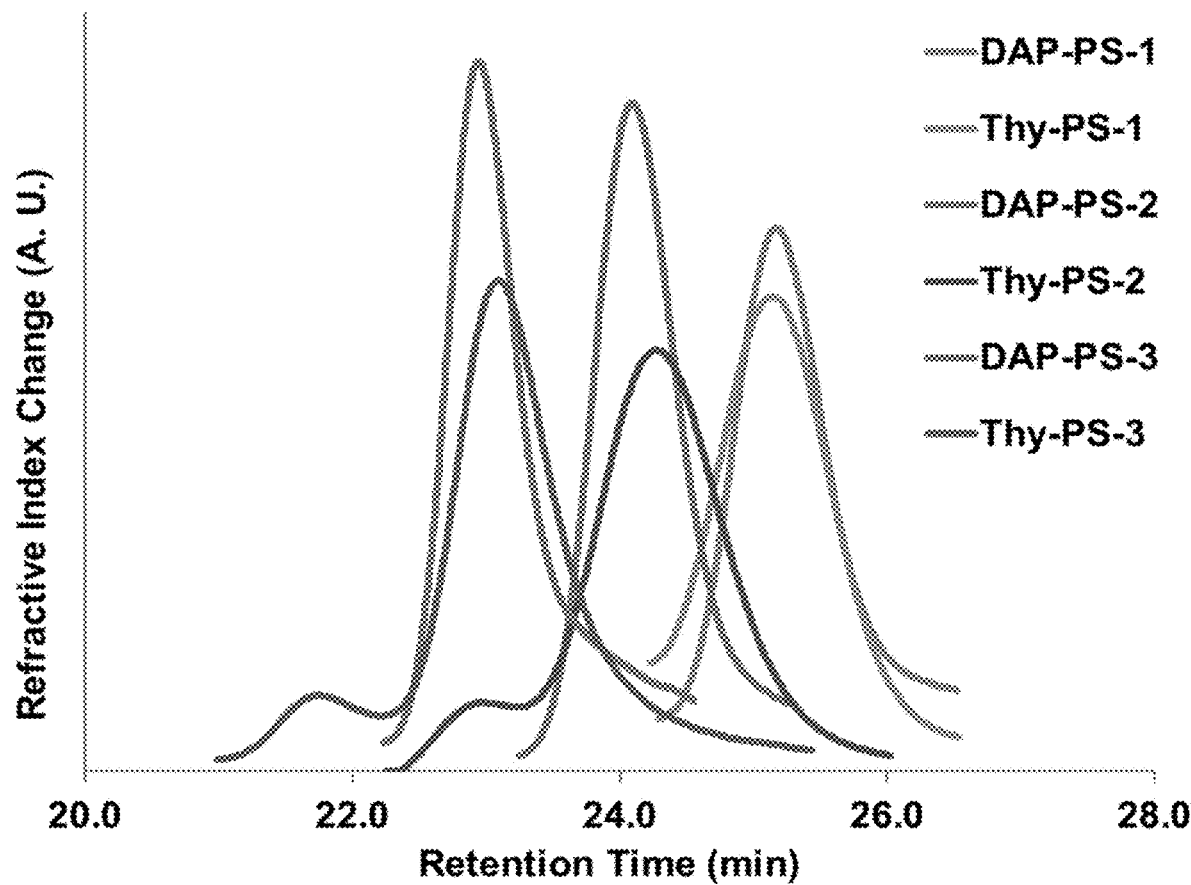
FIG. 6 shows a gel permeation chromatograph of diaminopyridine-polystyrene and thymine-polystyrene polymers, according to certain embodiments.

A nanocomposite tecton consists of a nanoparticle grafted with polymer chains that terminate in functional groups capable of supramolecular binding, where supramolecular interactions between polymers grafted to different particles enable programmable bonding that drives particle assembly (FIG. 4). Importantly, these interactions can be manipulated separately from the structure of the organic or inorganic components of the nanocomposite tecton, allowing for independent control over the chemical composition and spatial organization of all phases in the nanocomposite via a single design concept. Functionalized polystyrene polymers were made from diaminopyridine or thymine modified initiators via atom transfer radical polymerization, followed by post-functionalization to install a thiol group that allowed for particle attachment (FIG. 5). The polymers synthesized had three different molecular weights (~3.7, ~6.0, and ~11.0 kDa), as shown in FIG. 6, with narrow dispersity (Đ<1.10), and were grafted to nanoparticles of different diameters (10, 15, 20, and nm) via a "grafting-to" approach.

Once synthesized, nanocomposite tectons were functionalized with either diaminopyridine-polystyrene or thymine-polystyrene were readily dispersed in common organic solvents such as tetrahydrofuran, chloroform, toluene, and N,N'-dimethylformamide with a typical plasmonic resonance extinction peak at 530-540 nm (FIG. 7A) that confirmed their stability in these different solvents. Upon mixing, diaminopyridine-polystyrene and thymine-polystyrene coated particles rapidly assembled and precipitated from solution, resulting in noticeable red-shifting, diminishing, and broadening of the extinction peak within 1-2 minutes (example with 20 nm gold nanoparticles and 11.0 kDa polymers, FIG. 7B). Within 20 minutes, the dispersion appeared nearly colorless, and large, purple aggregates were visible at the bottom of the tube. After moderate heating (~55° C. for ~1-2 minutes for the example in FIG. 7B), the nanoparticles redispersed and the original color intensity was regained, demonstrating the dynamicity and complete reversibility of the diaminopyridine-thymine directed assembly process. Nanocomposite tectons were taken through multiple heating and cooling cycles without any alteration to assembly behavior or optical properties, signifying that they remained stable at each of these thermal conditions (FIG. 7C).

A key feature of the nanocomposite tectons is that the sizes of their particle and polymer components can be easily modified independent of the supramolecular binding group's molecular structure. However, because this assembly process is driven via the collective interaction of multiple diaminopyridine and thymine-terminated polymer chains, alterations that affect the absolute number and relative density of diaminopyridine or thymine groups on the nanocomposite tecton surface impact the net thermodynamic stability of the assemblies. In other words, while all constructs should be thermally reversible, the temperature range over which particle assembly and disassembly occurs should be affected by these variables. To better understand how differences in nanocomposite tecton composition impact the assembly process, nanostuctures were synthesized using different nanoparticle core diameters (10-40 nm) and polymer spacer molecular weights (3.7-11.0 kDa), and allowed to fully assemble at room temperature (~22° C.) (FIG. 8). Nanocomposite tectons were then monitored using UV-Vis spectroscopy at 520 nm while slowly heating at a rate of 0.25° C./min, resulting in a curve that clearly shows a characteristic disassembly temperature (melting temperature, $T_m$) for each nanocomposite tecton composition.

Figures 8A, 8B:
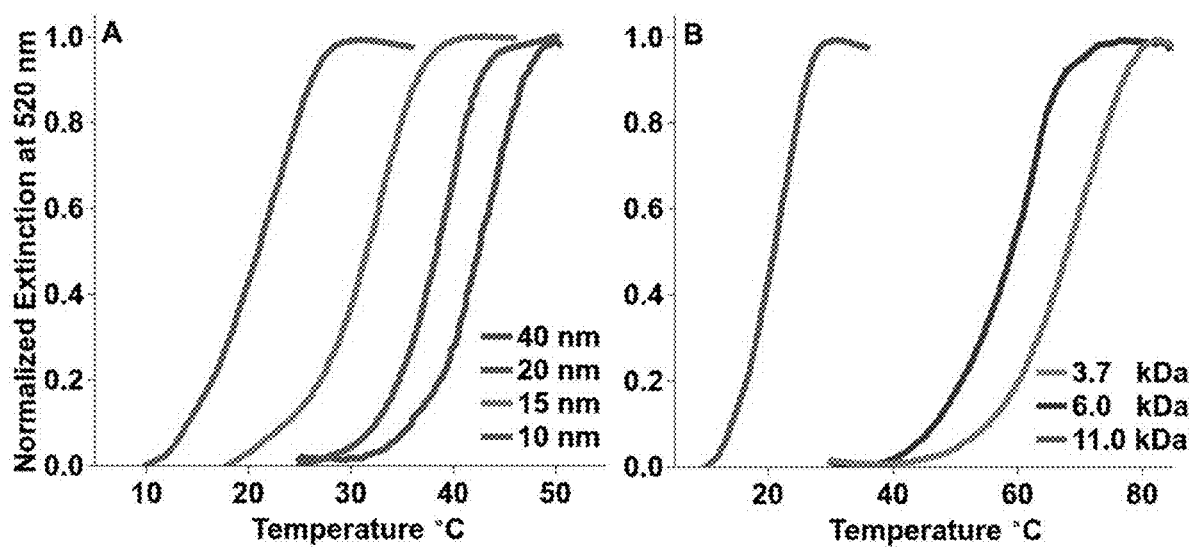
FIG. 8A shows a graph of normalized extinction versus temperature, according to certain embodiments.
FIG. 8B shows a graph of normalized extinction versus temperature, according to certain embodiments.

From these data, two clear trends can be observed. First, when holding polymer molecular weight constant, $T_m$ increases with increasing particle size (FIG. 8A). Conversely, when keeping particle diameter constant, $T_m$ drastically decreases with increasing polymer length (FIG. 8B). To understand these trends, it is important to note that nanocomposite tecton dissociation is governed by a collective and dynamic dissociation of multiple individual diaminopyridine-thymine bonds, which reside at the periphery of the polymer-grafted nanoparticles. The enthalpic component of nanocomposite tecton bonding behavior is therefore predominantly governed by the local concentration of the supramolecular bond-forming diaminopyridine and thymine groups, while the entropic component is dictated by differences in polymer configuration in the bound versus unbound states.

Figure 9:
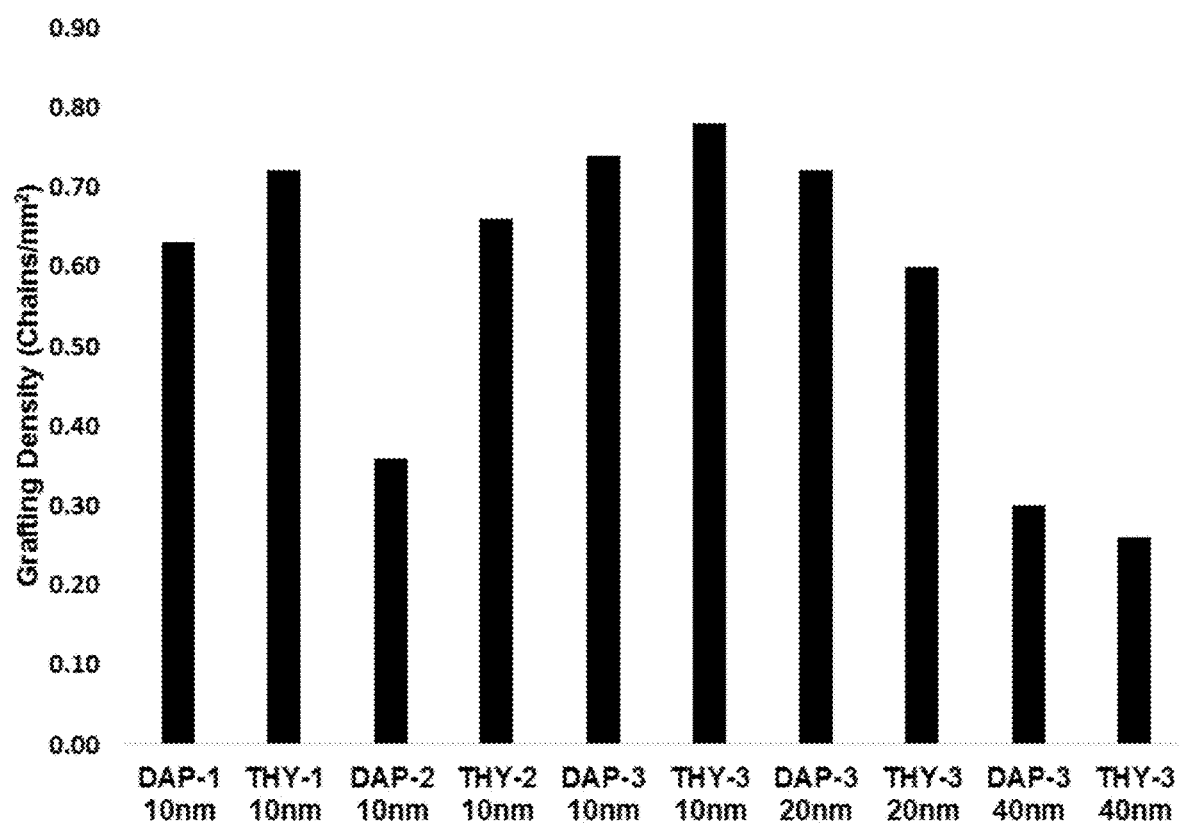
FIG. 9 shows, according to some embodiments, loading density of different nanostructures based on thermal gravimetric analysis data.

All nanocomposite tectons possess similar polymer grafting densities (i.e. equivalent areal density of polymer chains at the inorganic nanoparticle surface, FIG. 9) regardless of particle size or polymer length. However, the areal density of diaminopyridine and thymine groups at the periphery of the nanocomposite tectons is not constant as a function of these two variables due to nanocomposite tecton geometry.

When increasing inorganic particle diameter, the decreased surface curvature of the larger particle core forces the polymer chains into a tighter packing configuration, resulting in an increased areal density of diaminopyridine and thymine groups at the nanocomposite tecton periphery; this increased concentration of binding groups therefore results in an increased $T_m$, explaining the trend in FIG. 8A.

Conversely, for a fixed inorganic particle diameter (and thus constant number of polymer chains per particle), increasing polymer length decreases the areal density of diaminopyridine and thymine groups at the nanocomposite tecton periphery due to the "splaying" of polymers as they extend off of the particle surface, thereby decreasing $T_m$ in a manner consistent with the trend in FIG. 8B. Additionally, increasing polymer length results in a greater decrease of system entropy upon nanocomposite tecton assembly, due to the greater reduction of polymer configurations once the polymer chains are linked via a diaminopyridine-thymine bond; this would also be predicted to reduce T m. Within the temperature range tested, all samples were easily assembled and disassembled via alterations in temperature. Inorganic particle diameter and polymer length are therefore both effective handles to control nanocomposite tecton assembly behavior.

Figure 10:
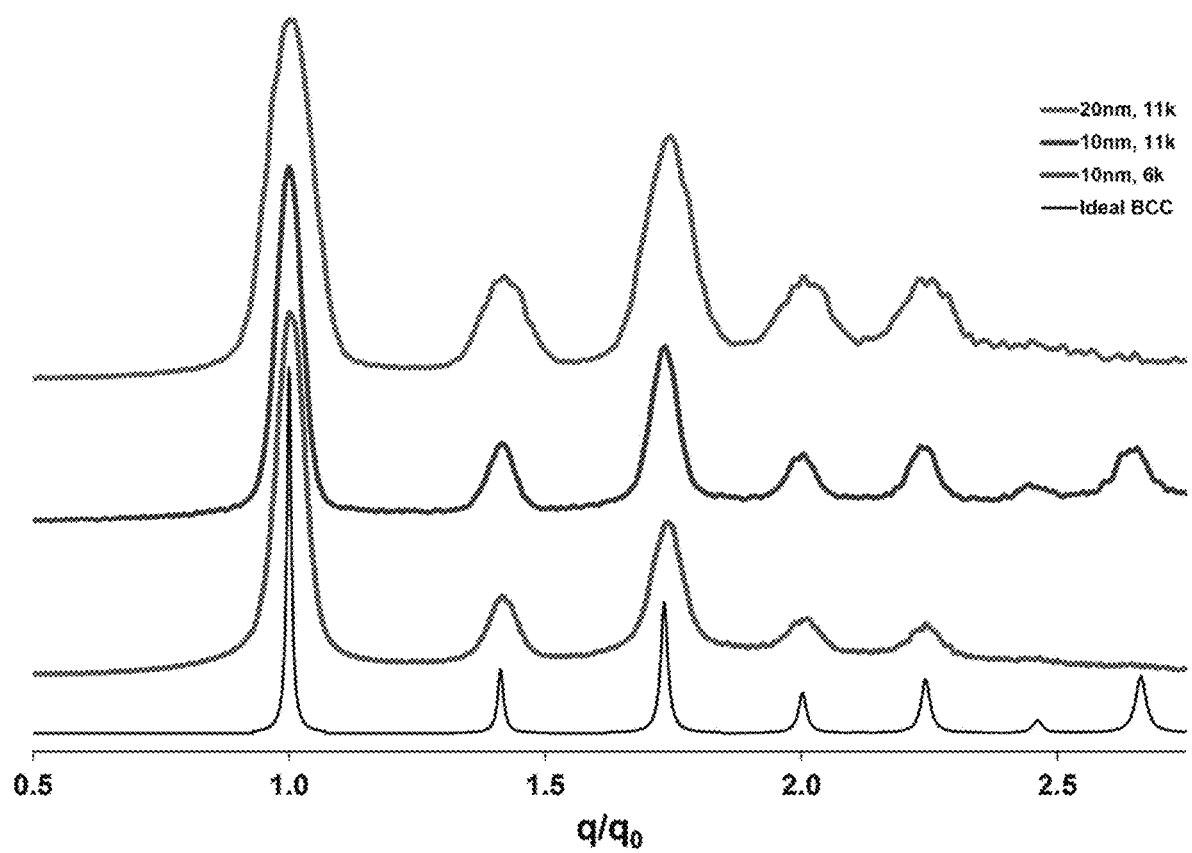
FIG. 10 shows small angle X-ray scattering data normalized as a function of $q_0$ scattering vectors for varying particle diameter and polymer molecular weight, according to some embodiments.

Importantly, because the nanocomposite tecton assembly process is based on dynamic, reversible supramolecular binding, it should be possible to drive the system to an ordered equilibrium state where the maximum number of binding events can occur. The particle cores and polymer ligands are polydisperse (FIG. 10) and ordered arrangements represent the thermodynamically favored state for a set of assembled nanocomposite tectons. When packing nanocomposite tectons into an ordered lattice, deviations in particle diameter would be expected to generate inconsistent particle spacings that would decrease the overall stability of the assembled structure. However, the inherent flexibility of the polymer chains should allow the nanocomposite tectons to adopt a conformation that compensates for these structural defects. As a result, an ordered nanocomposite tecton arrangement would still be predicted to be stable if it produced a larger number of diaminopyridine-thymine binding events than a disordered structure and this increase in binding events outweighed the entropic penalty of reduction in polymer chain configurations.

Figure 11:
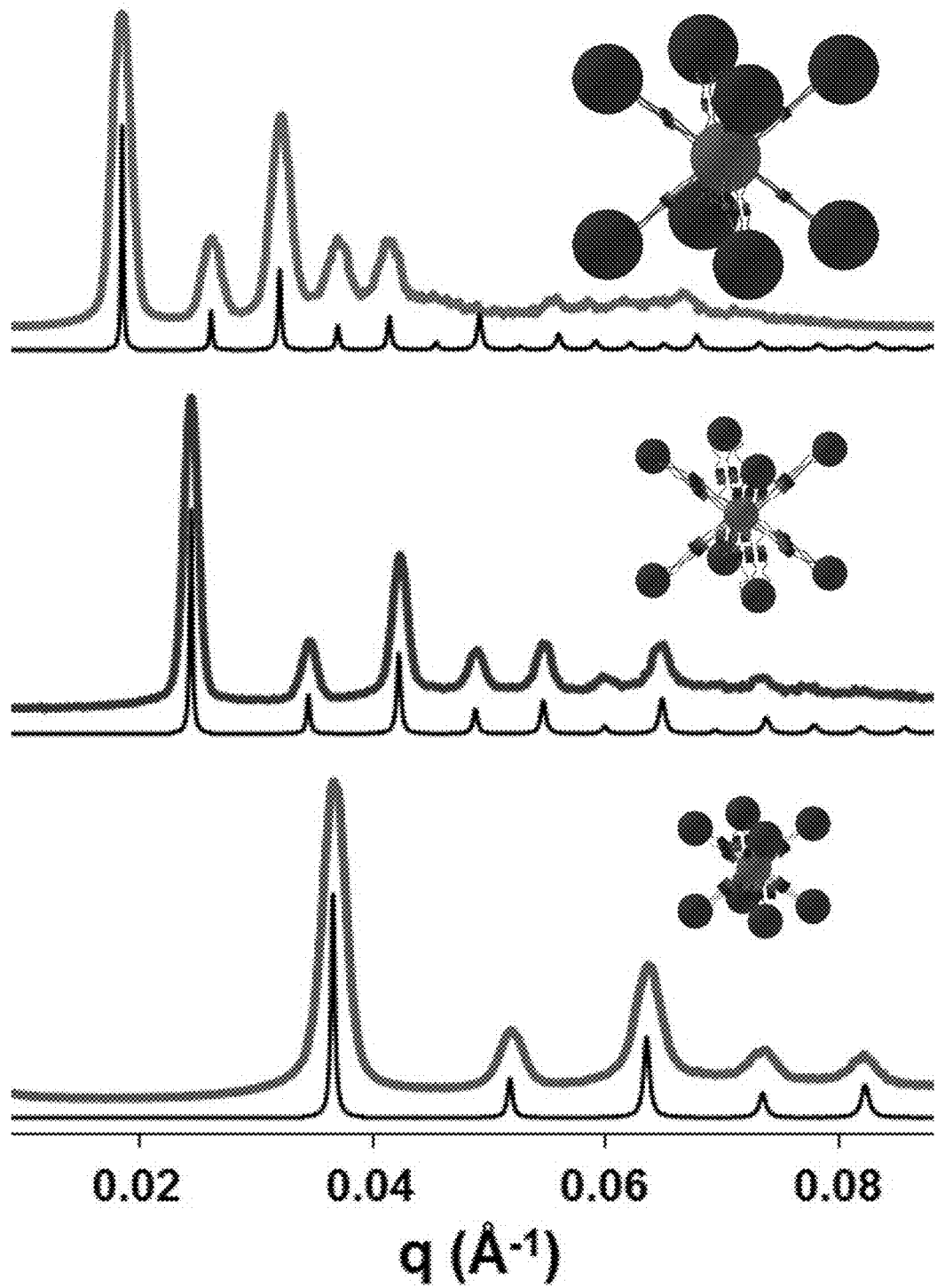
FIG. 11 shows small angle X-ray scattering data showing nanostructure assembly into ordered body-centered cubic lattice for varying particle diameter and polymer molecular weight, according to some embodiments.
Figure 12:
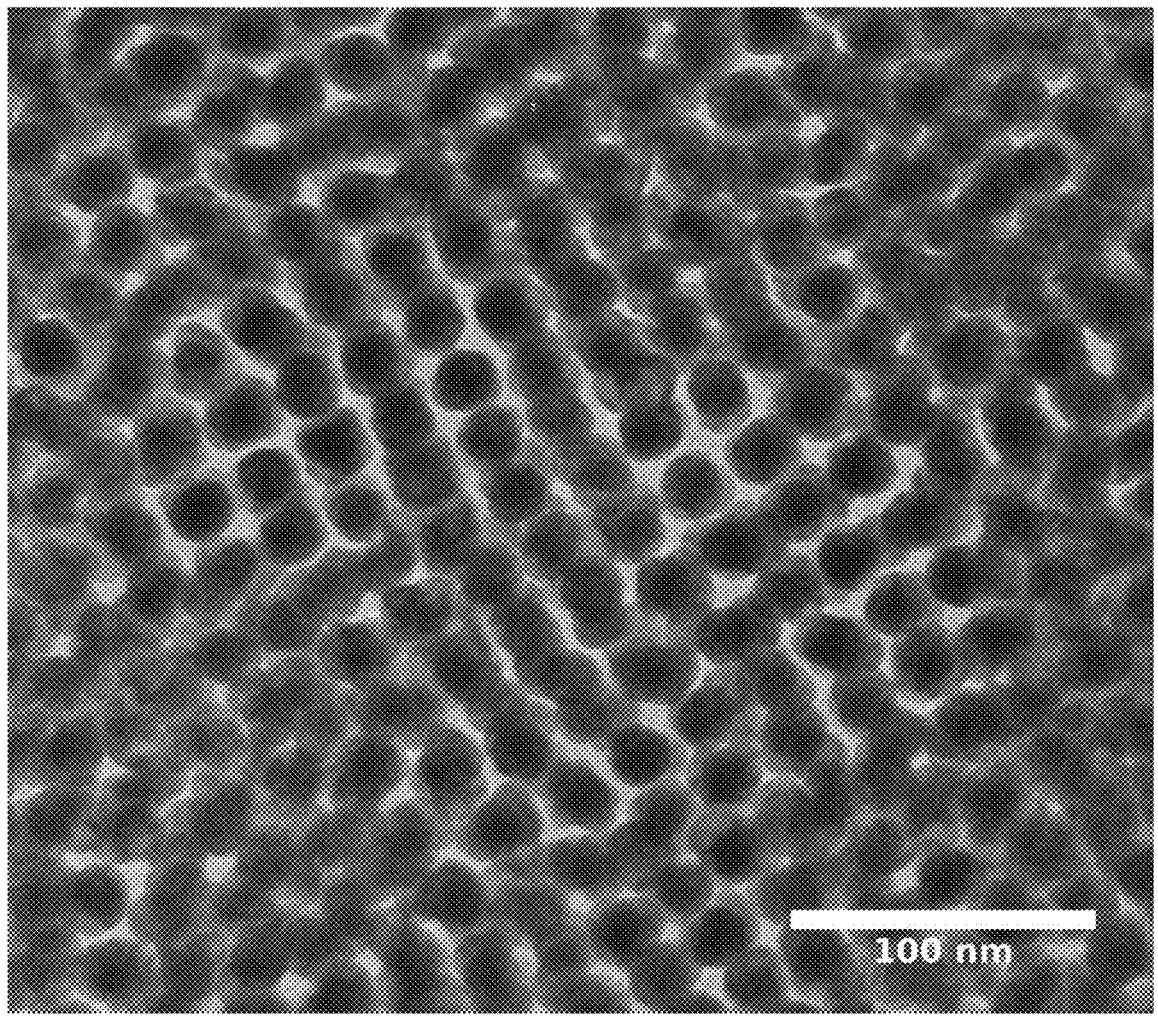
FIG. 12 shows, according to some embodiments, a transmission electron microscopy micrograph of nanostructures with 20 nm gold nanoparticles and 11.0 kDa polystyrene.

To test this hypothesis, multiple sets of assembled nanocomposite tectons were thermally annealed at a temperature just below their $T_m$, allowing particles to reorganize via a series of binding and unbinding events until they reached the thermodynamically most stable conformation. The resulting structures were analyzed with small angle X-ray scattering, revealing the formation of highly ordered mesoscale structures where the nanoparticles were arranged in body-centered cubic superlattices (FIG. 11). The body-centered cubic structure was observed for multiple combinations of particle size and polymer length, indicating that the nanoscopic structure of the composites can be controlled as a function of either the organic component (via polymer length), the inorganic component (via particle size), or both, making this nanocomposite tecton scheme a highly tailorable method for the design of future nanocomposites.

Example 2

The diaminopyridine-initiator was synthesized by first dissolving 5.5 g of 2,6-diaminopyridine (50 mmol) in 40 mL dry tetrahydrofuran in a 3-necked round bottom flask. At 0° C., the solution of 1.96 g (25 mmol) acetyl chloride in 15 mL dry tetrahydrofuran was added dropwise under a nitrogen atmosphere. The reaction mixture was allowed to warm to room temperature and stirred for 12 hours. The insoluble content was filtered off, and the solvent was removed under reduced pressure. The resulting solid was recrystallized in a mixture of ethanol and toluene, to afford 1 (FIG. 5) as a white solid (52%).

Next, 1.9 g of 1 in FIG. 5 (12.6 mmol) was dissolved in 80 mL dichloromethane, and then 3.5 mL trimethylamine (25 mmol) was added. The mixture was cooled to 0° C., and a solution of 3.22 g 2-bromoisobutyryl bromide (17.6 mmol) in dichloromethane (~10 mL) was added dropwise under a nitrogen atmosphere. The reaction mixture was allowed to warm to room temperature and stirred for 12 hours. The insoluble content was filtered off, and the filtrate was washed with a sodium carbonate solution (×1) and saline (×3). The organic phase was dried over sodium sulfate, the solvent was removed under reduced pressure, and the product was then purified by flash chromatography (methylene chloride/ethyl acetate 4:1). The product was further purified by recrystallization in methylene chloride/ethyl acetate/hexanes to afford the diaminopyridine-initiator (79%).

The thymine-initiator was synthesized by addition of 5.0 g thymine (40 mmol), 1.0 g 11-bromo-1-undecanol (4 mmol), 1.1 g potassium carbonate (8 mmol) and 200 mL dimethyl sulfoxide to a 500 mL round bottom flask. The mixture was stirred and bubbled with nitrogen for 2 minutes, and then sealed with a septum and stirred for 48 hours. The resulting mixture was poured into water and chloroform for extraction, and the organic phase was collected and washed 3 more times with brine, followed by drying over sodium sulfate and removal of solvent. The resulting white solid was recrystallized in ethyl acetate/hexanes to afford compound 2 in FIG. 5 (84%).

With the help of very gentle heat, 592 mg 2 in FIG. 5 (2 mmol) was dissolved in 150 mL dichloromethane, and 0.39 mL trimethylamine (2.8 mmol) was added to the solution. The mixture was cooled to 0° C., and a solution of 552 mg 2-bromoisobutyryl bromide (2.4 mmol) in dichloromethane (~10 mL) was added dropwise under a nitrogen atmosphere. The reaction mixture was allowed to warm to room temperature and stirred for 14 hours, and then washed with sodium carbonate (×2) and brine (×2). The organic phase was dried with sodium sulfate, and the solvent was removed under reduced pressure. The resulting mixture was purified by flash chromatography (methylene chloride/ethyl acetate 8:3), to afford the product ($R_f$=0.4) thymine-initiator as an off-white solid.

In a typical polymerization process, diaminopyridine-initiator (1.0 eq), tris[2-(dimethylamino)ethyl]amine (1.2 eq), styrene (100-200 eq. depending on target molecular weight), and anhydrous dimethylformamide (1:1 v/v to styrene) were added to an oven-dried and nitrogen filled Schlenk flask. The reaction flask was then sealed with a rubber septum and the mixture was taken through 3 freeze-pump-thaw cycles and refilled with nitrogen. Once the mixture returned to room temperature, the septum was removed, copper(I) bromide (1.2 eq) was quickly added against a positive nitrogen flow, and the flask was immediately resealed. The mixture was stirred at 110° C. under a nitrogen atmosphere, and quenched at different time points to give polystyrene of different molecular weights. The typical reaction time was 1-4 hours. To quench the reaction, the reaction mixture was poured into cold methanol, and the precipitated polymer was collected, redissolved in dichloromethane, and precipitated in methanol again to afford the polymer with a chain-end bromine.

Purified polystyrene obtained from diaminopyridine initiator was then dissolved in dimethylformamide (~10 mg/mL) with a small amount of trimethylamine (40 eq), and the solution was bubbled with nitrogen for 5 minutes, followed by the addition of 2-aminoethanethiol (15 eq). The reaction flask was capped, and the solution was stirred for 60 hours, then poured into a mixture of dichloromethane and brine. The organic phase was washed with brine repeatedly (×3), concentrated, and precipitated in methanol (redissolve-precipitate ×4). The resulting white powder was dried under vacuum to give the diaminopyridine-polystyrene polymer.

In a typical polymerization process, thymine-initiator (1 eq.), N,N,N',N",N"-pentamethyldiethylenetriamine (1 eq.), styrene (200 eq.), and anhydrous anisole (30 v % to styrene) were added to an oven-dried and nitrogen filled Schlenk flask. The reaction flask was then sealed with a rubber septum and the mixture was taken through 3 freeze-pump-thaw cycles and refilled with nitrogen. Once the mixture returned to room temperature, the septum was removed, copper(I) bromide (1 eq.) was quickly added against a positive nitrogen flow, and the flask was immediately resealed. The mixture was stirred at 110° C. under a nitrogen atmosphere, and quenched at different time points to give polystyrene of different molecular weights. The typical reaction time was 1-3 hours. To quench the reaction, the reaction mixture was poured into cold methanol, and the precipitated polymer was collected, redissolved in dichloromethane, and precipitated in methanol again to afford the polymer with a chain-end bromine.

The polymer was subsequently dissolved in dimethylformamide (— 10 mg/mL) with small amount of trimethylamine (40 eq.), and the solution was bubbled with nitrogen for 5 minutes, followed by the addition of 2-aminoethanethiol (15 eq.). The reaction flask was capped, and the solution was stirred for 60 hours, then poured into a mixture of dichloromethane and brine. The organic phase was washed with brine repeatedly (×3), concentrated, and precipitated in methanol (redissolve-precipitate ×4). The resulting white powder was dried under vacuum to give the thymine-polystyrene polymer.

In a typical synthetic process, an appropriate amount of diaminopyridine-polystyrene or thymine-polystyrene polymers was dissolved in 5.0 mL of acetone in a glass vial to yield a $1.3*10^{-4}$ M solution. The solution was vigorously stirred while 5.0 mL of gold nanoparticle solution was quickly poured into the vial, and the resulting suspension was allowed to stir for 1 hour. After the formation of dark red precipitate on the wall and at the bottom of the vial, the colorless supernatant was removed by direct decantation or with the aid of light centrifugation. Dimethylformamide (5-6 mL) was added to the vial to redisperse the precipitate, and the resulting dispersion was distributed in centrifuge tubes and purified for 3 centrifuge cycles. The centrifuge protocols were mainly determined by the particle size, while the polymer length had very limited influence. The solvents used to redisperse the gold nanoparticle precipitate at the end of each cycle were dimethylformamide, toluene, and toluene, respectively, and the final toluene dispersions were used for the self-assembly experiments.

Example 3

Nanocomposite tectons in this example were synthesized with gold nanoparticle cores, as the plasmon resonance of gold nanoparticles serves as an optical indicator of the assembly state of nanocomposite tectons. Free nanocomposite tectons exhibit maximum absorption at ~520 nm, while assembled nanocomposite tectons exhibit a red-shifted and broadened plasmon resonance at ~650 nm. In a typical "melt" experiment, a solution of assembled nanocomposite tectons was slowly heated to break the hydrogen bonds while the solution extinction was monitored with a spectrophotometer to determine the concentration of freely dispersed nanocomposite tectons. If the annealing is performed slowly, the nanocomposite tectons reach equilibrium at each temperature, and so the normalized melt curve is a close approximation of the fraction of dispersed nanocomposite tectons (f).

The nanocomposite tecton equilibrium constant ($K_M$) is related to f as:

$$f = \frac{1}{1 + K_M^{-1/2}} \quad (1)$$

Nanocomposite tectons are thermally active, and so it is useful to define a melting temperature ($T_M$) as the inflection point in the melt curve to characterize their transition between the two states. Furthermore, the equilibrium constant can be expressed in terms of the van't Hoff formula to relate the fraction of dispersed nanocomposite tectons to $\Delta H_M$ (Equation 2). The $\Delta H_M$ can be conveniently expressed in terms of T M and the derivative of f at $T_M$ (Equation 3) to determine $\Delta H_M$.

$$f = \frac{1}{1 + e^{\frac{\Delta H_M}{2R}*(\frac{1}{T}-\frac{1}{T_M})}} \quad (2)$$

$$\Delta H_M = 8RT_M^2 \frac{df}{dT_{T=T_M}} \quad (3)$$

Figure 13A:
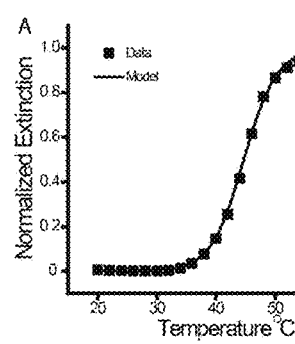
FIG. 13A shows, according to some embodiments, melt data for nanostructures with 26 nm gold nanoparticles and 12 kDa polymer.
Figure 13B:
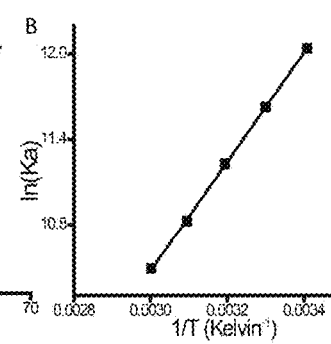
FIG. 13B shows an Arrhenius plot of the complexation of small molecule hydrogen bonding analogues measured in variable temperature $^1$H-NMR titrations, according to some embodiments.
Figure 13C:
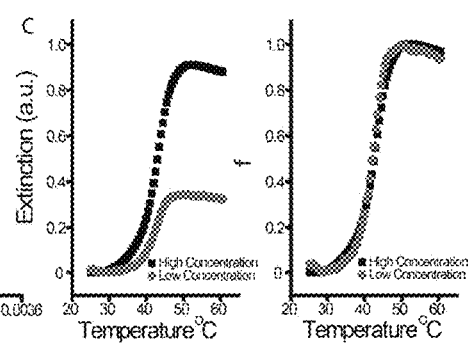
FIG. 13C shows, according to some embodiments, melt data for nanostructures performed at different concentrations (left) showing a similar thermodynamic response (right).

The experimental data matches the mathematical analysis well (FIG. 13A), with slight deviations due to irreversible deposition of nanocomposite tectons onto the walls of the cuvette, and thus provides a means to determine the binding enthalpy and entropy ($\Delta S_M=\Delta H_M/T_M$) of nanocomposite tecton assembly. As an additional point of comparison, two small molecules with the same supramolecular binding motifs were synthesized, and a variable temperature $^1$H-NMR titration was performed to measure the thermodynamic behavior of the supramolecular binding interaction isolated from the nanocomposite tecton geometry (FIG. 13B). The enthalpy of melting of the small molecule analogues, $\Delta H_S$, is 31.9 kJ/mol, which is much smaller than the $\Delta H_M$ determined for the sample in FIG. 14A, 628.6 kJ/mol. The large discrepancy in binding strength arises from the fact that nanocomposite tectons contain a large number of supramolecular bonds tightly packed on the nanocomposite tecton surface that can operate collectively. The cooperativity number, N, is defined as the ratio $\Delta H_M/\Delta H_S$, signifying the effective number of supramolecular bonds that are able to constructively act together. The implication of this is that unlike in conventional supramolecular systems, where the concentration of the binding pair strongly affects their binding strength, the relevant concentration for the nanocomposite tecton system is not of nanocomposite tectons in solution, but of the supramolecular binding groups on the periphery of the nanocomposite tecton. This is illustrated in FIG. 13C, where the melt curves of nanocomposite tectons at both high and low concentration are highly similar.

Figures 14A, 14B, 14C:
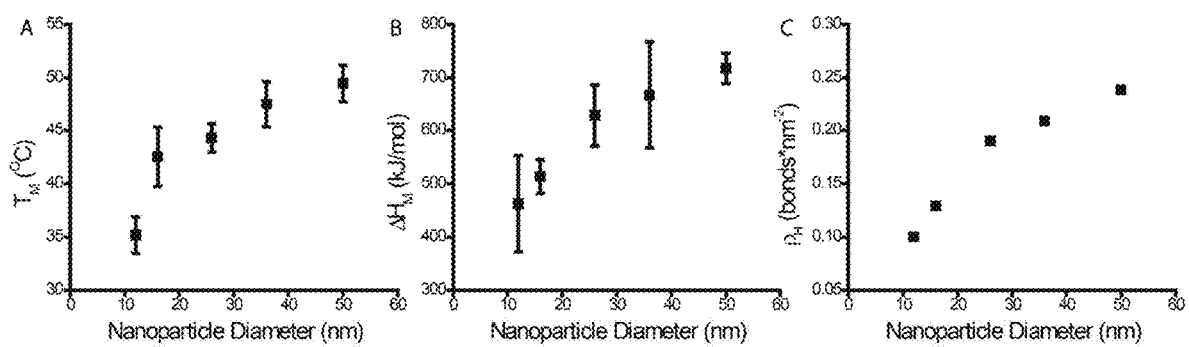
FIG. 14A shows, according to some embodiments, the melting temperature of intermolecular bonding groups of nanostructures with varying particle diameter and 12 kDa polymer.
FIG. 14B shows the enthalpy of melting of intermolecular bonding groups of nanostructures with varying nanoparticle diameter and 12 kDa polymer, according to some embodiments.
FIG. 14C shows, according to some embodiments, the concentration of intermolecular bonding groups of nanostructures with varying particle diameter and 12 kDa polymer.

A straightforward method for modifying the geometry of a nanocomposite tecton is to change the size of its nanoparticle core; gold nanoparticles with low dispersity were synthesized with 12, 16, 26, 36, and 50 nm diameters to study changes in thermodynamic behavior. After nanocomposite tectons were synthesized from these nanoparticles, melt experiments were performed to study their thermodynamic properties. As is shown in FIG. 14A, the melting temperature of the nanocomposite tectons increases with increasing particle size. This trend can be explained by an increase in the $\Delta H_M$ of the nanocomposite tecton assembly, which signifies an increase in the cooperativity of the supramolecular binding groups on the nanocomposite tecton surface (FIG. 14B). Because supramolecular chemistry is highly dependent on concentration, it was hypothesized that the local concentration of binding groups on the surface of the nanocomposite tecton would affect their cooperativity. Therefore, thermogravimetric analysis and dynamic light scattering measurements were performed in order to calculate the density of binding groups at the hydrodynamic surface of the nanocomposite tecton (pH), and it was established that the trend in $\Delta H_M$ and $T_M$ parallels the one in $\rho_H$ (FIG. 14C). This can be understood through a geometric argument, as the grafting density is not dramatically affected by particle size, the most significant difference between large and small particles is their surface curvature. The higher curvature of small particles results in a greater distance between binding groups, which lowers their likelihood to interact cooperatively. As the particles get larger, their curvature decreases, approaching the limit of a flat surface, producing a less rapid change in $\rho_H$. This result highlights the importance of local concentration, as opposed to total solution concentration, for nanocomposite tecton assembly, and how nanoscale geometry can be used to affect supramolecular chemistry.

Figure 15A:
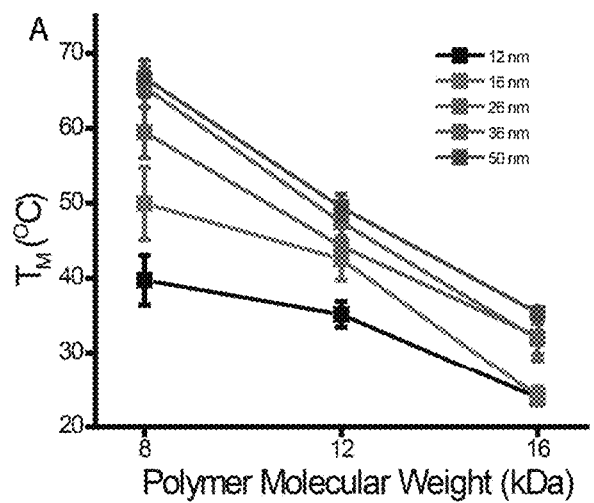
FIG. 15A shows, according to some embodiments, the dependence of $T_M$ of nanostructures on the molecular weight of the polymer.
Figure 15B:
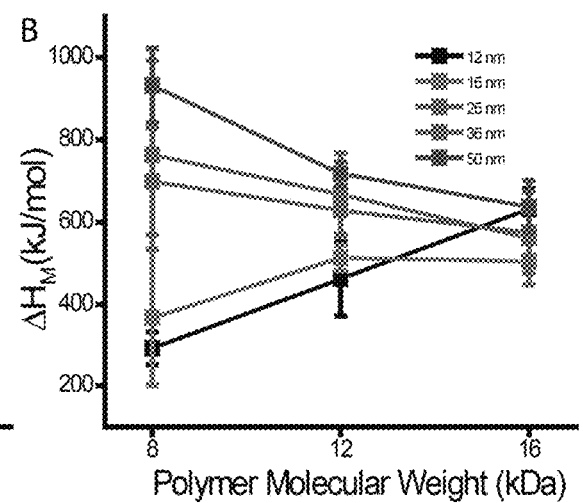
FIG. 15B shows, according to some embodiments, the enthalpy of melting of nanostructures on the molecular weight of the polymer.

In addition to changing the size of the nanoparticle core, the geometry of nanocomposite tectons can be manipulated by modifying the molecular weight of the polymer that comprises the outer corona of the nanocomposite tecton. Polymers of higher molecular weight extend further away from the nanoparticle core, increasing the surface area of the hydrodynamic sphere without modifying the number of polymer grafted to the gold nanoparticle surface, resulting in a decreased density of bonding groups from the previous analysis, lowering $\rho_H$ would be expected to weaken the association between complimentary nanocomposite tectons, and indeed the $T_M$ is diminished for nanocomposite tectons made with longer polymers (FIG. 15A). For the larger nanoparticle core sizes (26 nm, 36 nm, 50 nm), FIG. 15B shows the trend in $T_M$ corresponds with a decrease in $\Delta H_M$, and the value of $\Delta H_M$ appears to converge with longer polymers. This trend is consistent with the hypothesis that the thermodynamics of nanocomposite tecton assembly are highly dependent on surface concentration, and the convergence can be understood as the curvature effects of the core diminishing as the flexible polymer extends further away from it. However, the two smaller core diameter nanocomposite tectons (12 nm and 16 nm) show a surprising increase in $\Delta H_M$ with increasing polymer length, which suggests a more complex mechanism governs this effect.

Figure 15C:
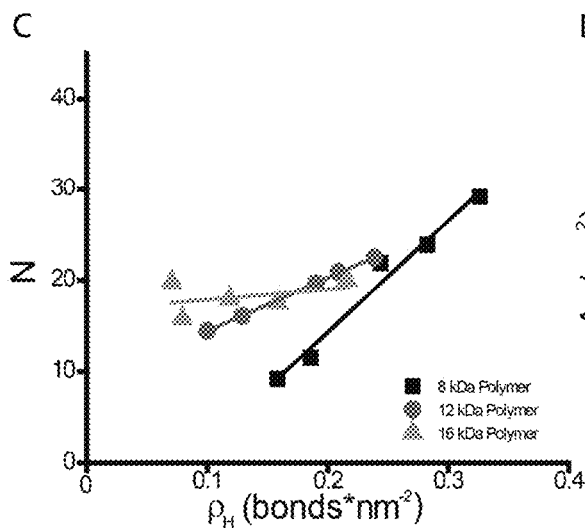
FIG. 15C shows changes in cooperativity with changing surface density of intermolecular bonding groups, according to some embodiments.

Greater clarity can be realized by examining how the cooperativity of the nanocomposite tecton assembly is impacted by changing the density of binding groups on the nanocomposite tecton surface (FIG. 15C). The cooperativity of the longest polymer does not show significant dependence on surface concentration, which is a result of the flexibility of the long polymer chains allowing for the cooperatively interacting supramolecular groups to still be brought together. The dependence of physical properties on the molecular weight of a polymer brush bears significant similarity to the previously described transition between the concentrated brush regime and the semi-dilute brush regime, where the density of polymer brushes is known to decrease as they extend off of curved particle surfaces and change the conformational behavior of the polymers. It is hypothesized that the shorter polymers exhibit concentrated polymer brush behavior and thus possess lower flexibility; alternatively, longer polymers on smaller particles begin to show some semi-dilute polymer brush character, which enables the polymer shell to deform to allow more supramolecular bonds to cooperatively interact while incurring a more significant entropic penalty. To further illustrate this, a bonding area representing the surface area of a nanocomposite tecton dedicated to cooperatively forming a bond between two nanocomposite tectons, $A_B$, can be calculated in units of nm$^2$ as:

$$A_B = \frac{N}{\rho_H} \quad (4)$$

where N represents the number of individual supramolecular bonds able to cooperatively interact with each other to bind together two complimentary nanocomposite tectons, and pH provides the density of supramolecular bonds along the hydrodynamic surface of the nanocomposite tecton.

Figure 15D:
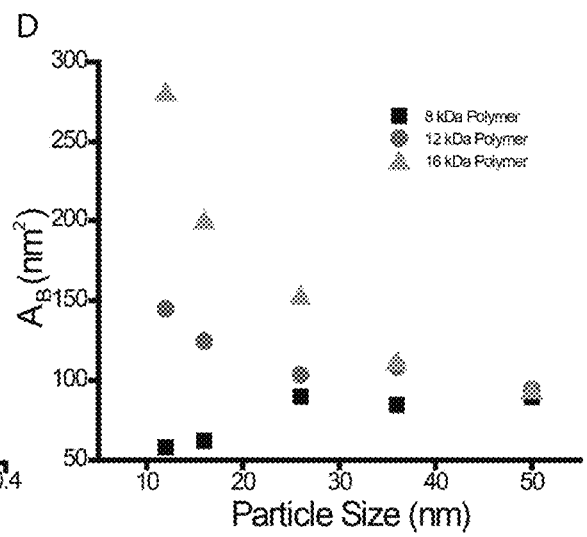
FIG. 15D shows the area on the surface of nanostructures that becomes engaged in cooperative bonding upon nanostructure assembly for varying particle diameter and polymer molecular weight, according to some embodiments.

In FIG. 15D, the area over which supramolecular binding groups are recruited for the long polymer case dramatically changes for smaller particle sizes which results in larger values of N than would be expected from the lower binding group density. However, as the polymer lengths get shorter, the cooperativity becomes more dependent on the surface density of binding groups. In these cases, the polymers in the more concentrated brush regime are not sufficiently flexible to modify their concentration of supramolecular binding groups, and so must balance the enthalpic gain from enhanced cooperativity with the entropic penalty for deforming the polymer chains. This can be further understood by examining $A_B$ for different polymer lengths in FIG. 15D. In comparison to the longer polymer, the 12 kDa and 8 kDa polymers are much less able to acquire supramolecular binding groups from across the surface of the nanocomposite tecton, and show smaller bonding areas for the smaller particle cores with lower surface concentrations. When considering the entirety of the $A_B$ data, it becomes evident that all three polymer lengths converge upon a bonding area of approximately 100 nm$^2$ at larger core diameters and more concentrated brush regimes. At these larger core diameters, and thus higher pH's, the polymer brush cannot be significantly densified by polymer deformation, and so the bonding area is instead limited by the distance that the cooperative effect is active over. Thus, although the bonding area does not dramatically change for the larger particles, pH does increase and thus the cooperativity still grows concatenately because the number of supramolecular binding groups within the area of the cooperative effect grows. It is further interesting that A B is smaller than the convergence area for the 8 kDa polymer on the smallest two particles, when for the other two polymer molecular weights $A_B$ increases on the smallest two particles. In those two cases the polymer is short enough that it cannot completely overcome the curvature of the nanoparticle core, still remaining in the concentrated brush regime and resulting in an even more diminished bonding area and cooperativity. In summary, although the T M of nanocomposite tecton assemblies appears to simply decrease with increasing polymer molecular weight, that decrease is the result of a complex balance between the enthalpy of the cooperative bonding and the conformational entropy of the polymer chains, all as a result of the unique geometry of nanocomposite tectons.

Figure 16A:
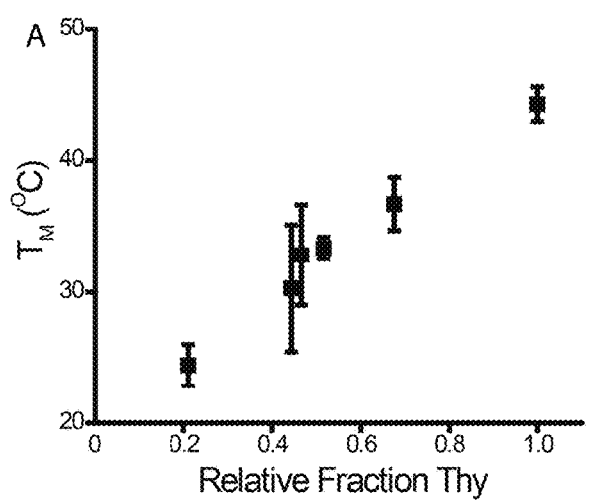
FIG. 16A shows, according to some embodiments, the effect of coloading thymine nanostructures with polymer on $T_M$.

Since the geometry of nanocomposite tectons can alter binding strength by controlling the local concentration of binding groups, a similar effect would be expected by decreasing pH by functionalizing nanocomposite tectons with a mixture of inert polystyrene and supramolecular binding group terminated polystyrene. To test this, samples were prepared by using mixtures of a defined feed ratio of inert and active polymer of equal molecular weights during the nanocomposite tecton synthesis process. This was found to significantly reduced the collective binding interaction between NCTs (at 50% coloading of the inert polymer, the melting temperature of the NCTs was below 22° C.) To diminish the effect of the coloading on reducing NCT collective bonding strength, coloaded thymine nanocomposite tectons were mixed with conventional diaminopyridine nanocomposite tectons, and it was observed that the $T_M$ dramatically decreases with small additions of inert polymer. This surprising result supports the hypothesis that the inert polymers are able to sterically interfere with the cooperativity of the supramolecular binding groups. In contrast, thymine nanocomposite tectons coloaded with varied feed ratios of short (4.4 kDa) inert polymer and longer (12 kDa) active polymer and assembled with conventional diaminopyridine nanocomposite tectons show melting transitions over experimentally accessible range (FIG. 16A). Furthermore, using multiple lengths of polymer solves the crucial experimental challenge of measuring the actual loading ratio on the particles, which can be done by decomposing the nanoparticle cores, recovering the polymer, and analyzing the two molecular weights as they pass through a gas permeation column.

Figure 16B:
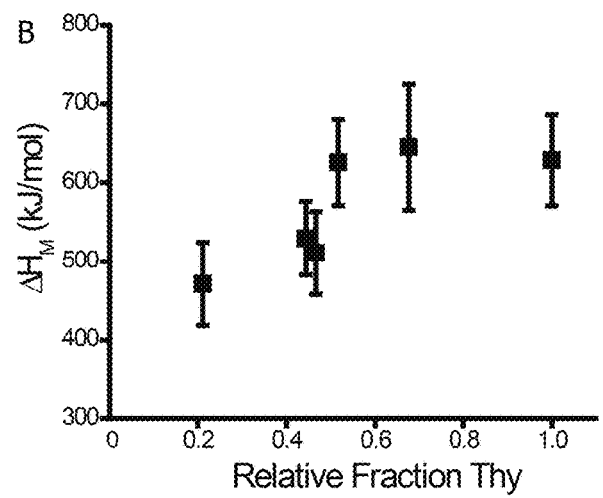
FIG. 16B shows, according to some embodiments, the effect of coloading thymine nanostructures with polymer on $\Delta H_M$.

In FIG. 16A, it can be seen that $T_M$ decreases directly with decreasing fractions of active polymer. As the coloading decreases the number of supramolecular bonding groups, it would be expected that this trend is due to decreasing the enthalpy of attraction between the two nanocomposite tectons. However, in FIG. 16B, $\Delta H_M$ slightly increases for small amounts of coloading, and decreases only for the samples with less than half as much active polymer as of pure nanocomposite tectons. When the nanocomposite tectons are coloaded with shorter polymers, their active polymers protruding from the nanocomposite tecton make a significantly less concentrated polymer coating, and so the slight increase in $\Delta H_M$ is analogous to the increase seen for high molecular weight polymers on smaller particles. In other words, the polymers gain more flexibility because they are more dilute, and so can more easily engage in bonding (FIG. 16C). However, the higher flexibility carries an entropic penalty, resulting in the decreased $T_M$. When the number of binding groups decreases to less than approximately half that of a pure nanocomposite tecton, $\Delta H_M$ does begin decreasing, which corresponds to the decreased density being sufficient enough to overwhelm the polymer flexibility and thereby decrease the cooperativity of the binding groups. The implication of these results is that simply changing the number of binding groups will not necessarily have the expected effect on supramolecular assembly, since such modifications will also alter the conformation of the polymers and so change the geometry of the nanocomposite tecton.

One last method of controlling nanocomposite tecton assembly is to modify the solvent in which they assemble. Supramolecular chemistry is known to be strongly affected by solvent, and the hydrogen bonding that attracts complimentary nanocomposite tectons is an electrostatic interaction, which are known to weaken in more polar solvents. In order to explore the behavior of nanocomposite tectons in different solvent media, melt experiments were performed in mixtures of toluene and 1,1,2,2 tetrachloroethane (TCE). TCE was chosen as the dopant solvent because it is a polar solvent that has a high boiling point, is available in a deuterated form, and does not contain any hydrogen bonding groups that could affect the nanocomposite tecton assembly process.

FIG. 17A shows the $T_M$ of nanocomposite tectons drops with increasing amounts of TCE up to 20 volume percent, which was the highest fraction at which reliable data could be collected due to parts of the melting curve dropping below room temperature. The most predictable explanation for the diminishing melting temperature would be that the more polar TCE lowers the $\Delta H_M$ of the nanocomposite tectons, but surprisingly FIG. 17B shows an increase in $\Delta H_M$ upon the addition of 5% TCE, though the resolution of the experiment is insufficient to determine with statistical significance if there is a further increase when more TCE is added. To better understand the change in bonding strength, variable temperature $^1$H-NMR titrations were performed on the small molecule diaminopyridine-thymine analogues in different solvent ratios (FIG. 17C). This data confirms the TCE does, in fact, decrease the binding strength of diaminopyridine-thymine bonds, but additionally and similar to the $T_M$ and $\Delta H_M$ data, the change is asymptotic as opposed to linear. The change in $T_M$, $\Delta H_M$, and $\Delta H_S$ would be linear if the TCE and toluene behaved as an ideal mixture in conjunction with the nanocomposite tectons, but the disproportionate effect on the assembly behavior of both the nanocomposite tectons and the small molecule analogs suggests the TCE preferentially solvates the supramolecular binding groups. Preferential solvation is often observed when a solute has much higher solubility in one component in a solvent mixture, and so the "good" solvent exists in higher concentration around the solute. Viewing nanocomposite tecton assembly through the lens of preferential solvation can provide insight into the peculiar $\Delta H_M$; since the TCE favorably interacts with diaminopyridine and thymine, it can better solvate them and augment the area their cooperative effect acts over. FIG. 17D demonstrates that adding TCE increases the cooperativity of the nanocomposite tectons. This understanding of adding TCE to the assembly suggests that the inter-nanocomposite tecton connections consist of a larger number of weaker supramolecular bonds, which raises $\Delta H_M$ (although that increase becomes very subtle as the two phenomena compete against each other), but lowers $T_M$ as entropy increases relative to the enthalpy. The physical response of nanocomposite tectons to additional solvents is not particularly surprising, but understanding the thermodynamic mechanism of that assembly is not intuitive and requires a thorough understanding of the geometry of nanocomposite tectons.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:
1. An article, comprising:
 a first component comprising a first particle, first polymers, and first intermolecular bonding groups, wherein each first polymer is associated with the first particle and at least one first intermolecular bonding group; and
 a second component comprising a second particle, second polymers, and second intermolecular bonding groups, wherein each second polymer is associated with the second particle and at least one second intermolecular bonding group,
 wherein at least a portion of the first intermolecular bonding groups are bonded to at least a portion of the second intermolecular bonding groups, and wherein at least one of the first intermolecular bonding groups does not comprise a moiety that is the same as a repeat unit or precursor thereof in the first polymers, and
 wherein a bond strength between at least the portion of the first intermolecular bonding groups and at least the portion of the second intermolecular bonding groups is greater than or equal to about 20 kJ/mol and less than or equal to about 100 kJ/mol.

2. An article, comprising:
a first component comprising a first particle, first polymers, and first intermolecular bonding groups, wherein each first polymer is associated with the first particle and at least one first intermolecular bonding group; and
a second component comprising a second particle, second polymers, and second intermolecular bonding groups, wherein each second polymer is associated with the second particle and at least one second intermolecular bonding group,
wherein at least a portion of the first intermolecular bonding groups are reversibly bonded to at least a portion of the second intermolecular bonding groups, and wherein at least one of the first intermolecular bonding groups does not comprise a moiety that is the same as a repeat unit or precursor thereof in the first polymers.

3. The article of claim 2, wherein the article comprises a plurality of the first component.

4. The article of claim 2, wherein the article comprises a plurality of the second composition component.

5. The article of claim 2, wherein the first polymers are synthetic polymers.

6. The article of claim 2, wherein the article further comprises a solvent.

7. An article, comprising:
a first component comprising a first particle, first polymers, and first intermolecular bonding groups, wherein each first polymer is associated with the first particle and at least one first intermolecular bonding group;
a second component comprising a second particle, second polymers, and second intermolecular bonding groups, wherein each second polymer is associated with the second particle and at least one second intermolecular bonding group; and
a solvent,
wherein at least a portion of the first intermolecular bonding groups are bonded to at least a portion of the second intermolecular bonding groups, and wherein at least one of the first intermolecular bonding groups does not comprise a moiety that is the same as a repeat unit or precursor thereof in the first polymers, and
wherein a melting temperature of the first component is greater than a freezing point of the solvent and less than a boiling point of the solvent.

8. An article, comprising:
a first component comprising a first particle, first polymers, and first intermolecular bonding groups, wherein each first polymer is associated with the first particle and at least one first intermolecular bonding group;
a second component comprising a second particle, second polymers, and second intermolecular bonding groups, wherein each second polymer is associated with the second particle and at least one second intermolecular bonding group; and
a solvent,
wherein at least a portion of the first intermolecular bonding groups are bonded to at least a portion of the second intermolecular bonding groups, and wherein at least one of the first intermolecular bonding groups does not comprise a moiety that is the same as a repeat unit or precursor thereof in the first polymers, and
wherein a melting temperature of the second component is greater than a freezing point of the solvent and less than a boiling point of the solvent.

9. An article, comprising:
a first component comprising a first particle, first polymers, and first intermolecular bonding groups, wherein each first polymer is associated with the first particle and at least one first intermolecular bonding group;
a second component comprising a second particle, second polymers, and second intermolecular bonding groups, wherein each second polymer is associated with the second particle and at least one second intermolecular bonding group; and
a solvent,
wherein at least a portion of the first intermolecular bonding groups are bonded to at least a portion of the second intermolecular bonding groups, and wherein at least one of the first intermolecular bonding groups does not comprise a moiety that is the same as a repeat unit or precursor thereof in the first polymers, and
wherein a bond strength between the solvent and the second intermolecular bonding groups is less than a bond strength between at least the portion of the first intermolecular bonding groups and at least the portion of the second intermolecular groups.

10. An article, comprising:
a first component comprising a first particle, first polymers, and first intermolecular bonding groups, wherein each first polymer is associated with the first particle and at least one first intermolecular bonding group;
a second component comprising a second particle, second polymers, and second intermolecular bonding groups, wherein each second polymer is associated with the second particle and at least one second intermolecular bonding group; and
a solvent,
wherein at least a portion of the first intermolecular bonding groups are bonded to at least a portion of the second intermolecular bonding groups, and wherein at least one of the first intermolecular bonding groups does not comprise a moiety that is the same as a repeat unit or precursor thereof in the first polymers, and
wherein a bond strength between the solvent and the first intermolecular bonding groups is less than a bond strength between at least the portion of the first intermolecular bonding groups and at least the portion of the second intermolecular groups.

11. An article, comprising:
a first component comprising a first particle, first polymers, and first intermolecular bonding groups, wherein each first polymer is associated with the first particle and at least one first intermolecular bonding group; and
a second component comprising a second particle, second polymers, and second intermolecular bonding groups, wherein each second polymer is associated with the second particle and at least one second intermolecular bonding group,
wherein at least a portion of the first intermolecular bonding groups are bonded to at least a portion of the second intermolecular bonding groups, and wherein at least one of the first intermolecular bonding groups does not comprise a moiety that is the same as a repeat unit or precursor thereof in the first polymers, and
wherein a bond strength between at least a portion of the second polymers and the second intermolecular bonding groups is less than a bond strength between at least the portion of the first intermolecular bonding groups and at least the portion of the second intermolecular groups.

12. An article, comprising:
a first component comprising a first particle, first polymers, and first intermolecular bonding groups, wherein each first polymer is associated with the first particle and at least one first intermolecular bonding group; and
a second component comprising a second particle, second polymers, and second intermolecular bonding groups, wherein each second polymer is associated with the second particle and at least one second intermolecular bonding group,
wherein at least a portion of the first intermolecular bonding groups are bonded to at least a portion of the second intermolecular bonding groups, and wherein at least one of the first intermolecular bonding groups does not comprise a moiety that is the same as a repeat unit or precursor thereof in the first polymers, and
wherein a bond strength between at least a portion of the first polymers and the first intermolecular bonding groups is less than a bond strength between at least the portion of the first intermolecular bonding groups and at least the portion of the second intermolecular groups.

13. An article, comprising:
a first component comprising a first particle, first polymers, and first intermolecular bonding groups, wherein each first polymer is associated with the first particle and at least one first intermolecular bonding group; and
a second component comprising a second particle, second polymers, and second intermolecular bonding groups, wherein each second polymer is associated with the second particle and at least one second intermolecular bonding group,
wherein at least a portion of the first intermolecular bonding groups are bonded to at least a portion of the second intermolecular bonding groups, and wherein at least one of the first intermolecular bonding groups does not comprise a moiety that is the same as a repeat unit or precursor thereof in the first polymers, and
wherein a bond strength between at least a portion of the second polymers and the first intermolecular bonding groups is less than a bond strength between at least the portion of the first intermolecular bonding groups and at least the portion of the second intermolecular groups.

14. An article, comprising:
a first component comprising a first particle, first polymers, and first intermolecular bonding groups, wherein each first polymer is associated with the first particle and at least one first intermolecular bonding group; and
a second component comprising a second particle, second polymers, and second intermolecular bonding groups,
wherein each second polymer is associated with the second particle and at least one second intermolecular bonding group,
wherein at least a portion of the first intermolecular bonding groups are bonded to at least a portion of the second intermolecular bonding groups, and wherein at least one of the first intermolecular bonding groups does not comprise a moiety that is the same as a repeat unit or precursor thereof in the first polymers, and
wherein a bond strength between at least a portion of the first polymers and the second intermolecular bonding groups is less than a bond strength between at least the portion of the first intermolecular bonding groups and at least the portion of the second intermolecular groups.

15. The article of claim 2, wherein at least one of the second intermolecular bonding groups does not comprise a moiety that is the same as a repeat unit or precursor thereof in the second polymers.

16. The article of claim 11, wherein a bond strength between at least a portion of the first polymers and the first intermolecular bonding groups is less than the bond strength between at least the portion of the first intermolecular bonding groups and at least the portion of the second intermolecular bonding groups.

17. The article of claim 12, wherein a bond strength between at least a portion of the second polymers and the second intermolecular bonding groups is less than the bond strength between at least the portion of the first intermolecular bonding groups and at least the portion of the second intermolecular bonding groups.

18. The article of claim 13, wherein a bond strength between at least a portion of the first polymers and the second intermolecular bonding groups is less than the bond strength between at least the portion of the first intermolecular bonding groups and at least the portion of the second intermolecular bonding groups.

19. The article of claim 14, wherein a bond strength between at least a portion of the second polymers and the first intermolecular bonding groups is less than the bond strength between at least the portion of the first intermolecular bonding groups and at least the portion of the second intermolecular bonding groups.

20. The article of claim 1, wherein at least the portion of the first intermolecular bonding groups are reversibly bonded to at least the portion of the second intermolecular bonding groups.

* * * * *